United States Patent
Cooper et al.

(10) Patent No.: US 12,016,884 B2
(45) Date of Patent: Jun. 25, 2024

(54) ADIPOSE DERIVED STEM CELL EXOSOMES AND USES THEREOF

(71) Applicants: UNIVERSITY OF SOUTH FLORIDA, Tampa, FL (US); THE UNITED STATES DEPARTMENT OF VETERANS AFFAIRS, Washington, DC (US)

(72) Inventors: Denise R. Cooper, St. Petersburg, FL (US); Lisa Gould, Warwick, RI (US); Niketa Patel, Land O'Lakes, FL (US); Mack Wu, Tampa, FL (US)

(73) Assignees: UNIVERSITY OF SOUTH FLORIDA, Tampa, FL (US); THE UNITED STATES GOVERNMENT AS REPRESENTED BY THE DEPARTMENT OF VETERANS AFFAIRS, Washington, DC (US)

( * ) Notice: Subject to any disclaimer, the term of this patent is extended or adjusted under 35 U.S.C. 154(b) by 349 days.

(21) Appl. No.: 16/329,448

(22) PCT Filed: Aug. 30, 2017

(86) PCT No.: PCT/US2017/049359
§ 371 (c)(1),
(2) Date: Feb. 28, 2019

(87) PCT Pub. No.: WO2018/045022
PCT Pub. Date: Mar. 8, 2018

(65) Prior Publication Data
US 2019/0192576 A1 Jun. 27, 2019

Related U.S. Application Data

(60) Provisional application No. 62/381,054, filed on Aug. 30, 2016.

(51) Int. Cl.
| | | |
|---|---|---|
| A61K 35/35 | (2015.01) | |
| A61K 9/00 | (2006.01) | |
| A61P 17/02 | (2006.01) | |
| C12N 5/077 | (2010.01) | |
| C12N 5/0775 | (2010.01) | |
| C12N 15/113 | (2010.01) | |

(52) U.S. Cl.
CPC ............ A61K 35/35 (2013.01); A61K 9/0014 (2013.01); A61P 17/02 (2018.01); C12N 5/0653 (2013.01); C12N 5/0667 (2013.01); C12N 15/113 (2013.01); C12N 2310/111 (2013.01); C12N 2310/20 (2017.05)

(58) Field of Classification Search
None
See application file for complete search history.

(56) References Cited

U.S. PATENT DOCUMENTS

| | | |
|---|---|---|
| 2012/0093885 A1 | 4/2012 | Sahoo |
| 2014/0147454 A1 | 5/2014 | Chakraborty et al. |
| 2014/0371296 A1 | 12/2014 | Bennett et al. |
| 2015/0366897 A1 | 12/2015 | Stevanato et al. |
| 2016/0041153 A1 | 2/2016 | Brown et al. |

FOREIGN PATENT DOCUMENTS

| | | | | |
|---|---|---|---|---|
| KR | 20150145720 A | * | 12/2015 | ........... C12N 5/0667 |
| WO | WO-2013096837 A1 | * | 6/2013 | ........... C12N 15/113 |
| WO | WO2015022545 A2 | | 2/2015 | |
| WO | 2016072821 A1 | | 5/2016 | |
| WO | WO-2016072821 A1 | * | 5/2016 | ............. A61K 35/12 |
| WO | 2016089732 A2 | | 6/2016 | |

OTHER PUBLICATIONS

Trinh NT, Yamashita T, Tu TC, Kato T, Ohneda K, Sato F, Ohneda O. Microvesicles enhance the mobility of human diabetic adipose tissue-derived mesenchymal stem cells in vitro and improve wound healing in vivo. Biochem Biophys Res Commun. May 13, 2016;473(4):1111-1118. (Year: 2016).*

Tajiri et al. Intravenous transplants of human adipose-derived stem cell protect the brain from traumatic brain injury-induced neurodegeneration and motor and cognitive impairments: cell graft biodistribution and soluble factors in young and aged rats. J Neurosci. Jan. 1, 2014;34(1):313-26. (Year: 2014).*

Khorshidi A., Dhaliwal P., Yang B.B. (2016) Noncoding RNAs in Tumor Angiogenesis. In: Song E. (eds) The Long and Short Noncoding RNAs in Cancer Biology. Advances in Experimental Medicine and Biology, vol. 927. (Year: 2016).*

Liang X, Zhang L, Wang S, Han Q, Zhao RC. Exosomes secreted by mesenchymal stem cells promote endothelial cell angiogenesis by transferring miR-125a. J Cell Sci. Jun. 1, 2016;129(11):2182-9. (Year: 2016).*

Basu J, Ludlow JW. Exosomes for repair, regeneration and rejuvenation. Expert Opin Biol Ther. 2016;16(4):489-506. (Year: 2016).*

Ha D, Yang N, Nadithe V. Exosomes as therapeutic drug carriers and delivery vehicles across biological membranes: current perspectives and future challenges. Acta Pharm Sin B. Jul. 2016;6(4):287-96. (Year: 2016).*

Takahashi K, Yan IK, Wood J, Haga H, Patel T. Involvement of extracellular vesicle long noncoding RNA (linc-VLDLR) in tumor cell responses to chemotherapy. Mol Cancer Res. Oct. 2014;12(10):1377-87. (Year: 2014).*

Xiang J, Guo S, Jiang S, Xu Y, Li J, Li L, Xiang J. Silencing of Long Non-Coding RNA MALAT1 Promotes Apoptosis of Glioma Cells. J Korean Med Sci. May 2016;31(5):688-94. (Year: 2016).*

(Continued)

*Primary Examiner* — Teresa E Knight
(74) *Attorney, Agent, or Firm* — Quarles & Brady LLP

(57) ABSTRACT

Provided herein are exosomal compositions and exsosomal lncRNA compositions and formulations thereof. Also provided herein are methods of treating a wound in a subject in need thereof that can contain the step of administering an exosomal composition and/or exsosomal lncRNA compositions or formulation thereof to a wound in a subject in need thereof.

13 Claims, 18 Drawing Sheets

Specification includes a Sequence Listing.

(56) References Cited

OTHER PUBLICATIONS

Paralkar VR, Mishra T, Luan J, Yao Y, Kossenkov AV, Anderson SM, Dunagin M, Pimkin M, Gore M, Sun D, Konuthula N, Raj A, An X, Mohandas N, Bodine DM, Hardison RC, Weiss MJ. Lineage and species-specific long noncoding RNAs during erythro-megakaryocytic development. Blood. Mar. 20, 2014;123(12):1927-37. (Year: 2014).*

Igor Legen, Matjaž Kračun, Mateja Salobir, Janez Kerč, The evaluation of some pharmaceutically acceptable excipients as permeation enhancers for amoxicillin. 2006. vol. 308;issue 2, pp. 84-89 (Year: 2006).*

Mallory AC, Shkumatava A. LncRNAs in vertebrates: advances and challenges. Biochimie. Oct. 2015;117:3-14. (Year: 2015).*

Bels ER, Breakefield XO. Introduction to Extracellular Vesicles: Biogenesis, RNA Cargo Selection, Content, Release, and Uptake. Cell Mol Neurobiol. Apr. 2016;36(3):301-12. (Year: 2016).*

Peter Uetz. How Many Reptile Species? Herpetological Review. 2000. 13(1), 13-15 (Year: 2000).*

Guo S, Dipietro LA. Factors affecting wound healing. J Dent Res. Mar. 2010;89(3):219-29. (Year: 2010).*

Kim et al. Wound healing effect of adipose-derived stem cells: A critical role of secretory factors on human dermal fibroblasts. Journal of Dermatological Science (2007) 48, 15-24 (Year: 2007).*

Ojeh et al. Stem Cells in Skin Regeneration, Wound Healing, and Their Clinical Applications. Int. J. Mol. Sci. 2015, 16, 25476-25501 (Year: 2015).*

Li et al. Exosomal cargo-loading and synthetic exosome-mimics as potential therapeutic tools. Acta Pharmacologica Sinica (2018) 39: 542-551 (Year: 2018).*

Kruger et al. Comprehensive management of pressure ulcers in spinal cord injury: Current concepts and future trends. The Journal of Spinal Cord Medicine. vol. 36. No. 6. p. 572-585 (Year: 2013).*

International Search Report for PCT/US2017/049359 of Nov. 16, 2017.

Patel, et al. "Adipose-derived stem cells from lean and obese humans show depot specific differences in thier stem cell markers, exosome contents and senescence: role of protein kinase C delta in adipose stem cell niche," Stem Cell Investigation, Jan. 31, 2016, 3:2, p. 1-12.

Rani, et al., "The Exosome—A Naturally Secreted Nanoparticle and its Application to Wound Healing", Advanced Materials (Weinheim, Germany) (2015).

Shabbir, et al., "Mesenchymal Stem Cell Exosomes Induce Proliferation and Migration of Normal and Chronic Wound Fibroblasts, and Enhance Angiogenesis In Vitro", Stem Cells and Development (2015), 24, (14), 1635-1647.

Geiger, et al., "Human fibrocyte-derived exosomes accelerate wound healing in genetically diabetic mice", Biochemical and Biophysical Research Communications, vol. 467, Issue 2, Nov. 13, 2015, pp. 303-309.

* cited by examiner

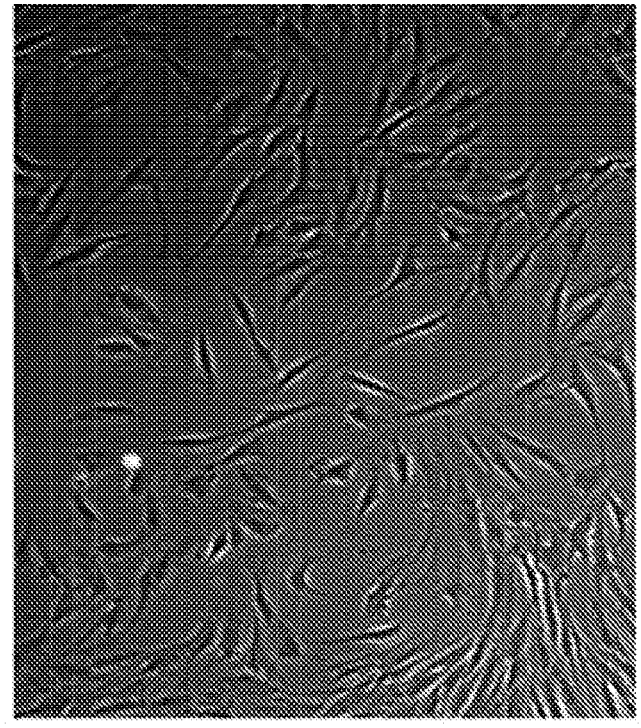
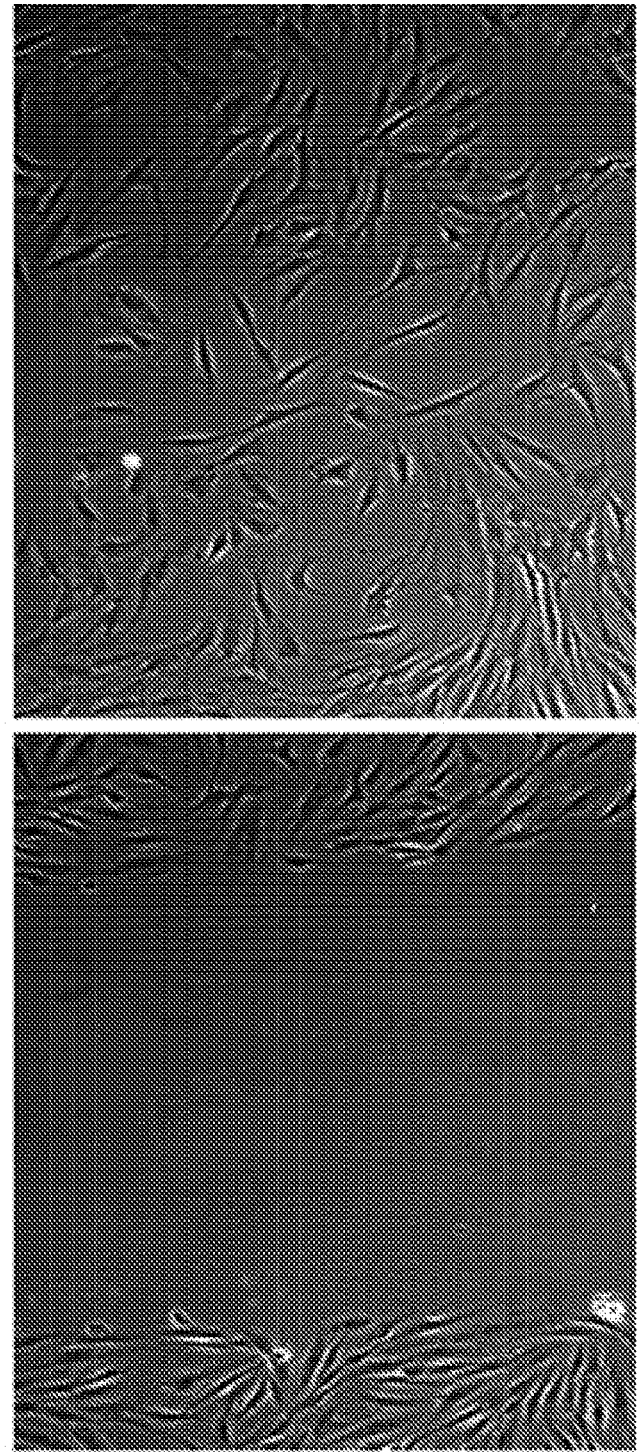
FIG. 2A 0hr
FIG. 2B 18hr
Unconditioned Medium

ADIPOSE DERIVED STEM CELL EXOSOMES AND USES THEREOF

CROSS-REFERENCE TO RELATED APPLICATIONS

This application is the 35 U.S.C. 0.371 national stage application of PCT Application No. PCT/US2017/049359, filed Aug. 30, 2017, where the PCT claims priority to, and the benefit of, U.S. provisional application entitled "ADIPOSE DERIVED STEM CELL EXOSOMES AND USES THEREOF" having Ser. No. 62/381,054, filed Aug. 30, 2016, both of which are herein incorporated by reference in their entireties.

STATEMENT REGARDING FEDERALLY SPONSORED RESEARCH OR DEVELOPMENT

This invention was made with government support under grant number HL 120954 awarded by the National Institutes of Health. The government has certain rights in the invention.

SEQUENCE LISTING

This application contains a sequence listing filed in electronic form as an ASCII.txt file entitled 292103-2780_ST25.txt, created on Aug. 30, 2017. The content of the sequence listing is incorporated herein in its entirety.

BACKGROUND

There is a rapidly growing cohort of older people, including veterans with diabetes and a new cohort of wounded people, including veterans, with injuries that include non-healing ulcers from spinal cord injury, multiple traumatic injuries, and burns. In particular, veteran and similar populations are at risk for a staggering number of chronic wounds. As such, there exists an unmet need for improved compositions and treatments for chronic wounds.

SUMMARY

Described herein are pharmaceutical formulations that can include an amount of adipose stem cell derived exosomes, wherein the exosomes can have an amount of MALAT1 lncRNA; and a pharmaceutically acceptable carrier. The amount of adipose stem cell derived exosomes can be an effective amount sufficient to increase the rate of wound healing. In some aspects, the effective amount can range from about 0.001 pg to about 500 µg. In some aspects, the effective amount can range from about 9 µg/mL to about 20 µg/mL.

Also described herein are pharmaceutical formulations that can include an amount of MALAT1, VLDLR, or GAS5 lncRNA; and a pharmaceutically acceptable carrier. The amount of MALAT1, VLDLR, or GAS5 lncRNA can be an effective amount sufficient to increase the rate of wound healing. In some aspects, the effective amount can range from about 0.001 pg to about 500 µg or more. In some aspects, the effective amount can range from about 0.001 pg/mL to about 500 µg/mL. In some aspects, the MALAT1 lncRNA can have a sequence that is about 95-100% identical to SEQ ID NO.: 1 or is a fragment of at least 20 contiguous nucleotides that are 95-100% identical to SEQ ID NO: 1, the VLDLR lncRNA can have a sequence that is about 90-100% identical to SEQ ID NO.: 2 or can be a fragment of at least 20 contiguous nucleotides that can be about 95-100% identical to SEQ ID NO: 2; and the GAS5 lncRNA can have a sequence that is 90-100% about identical to SEQ ID NO.: 3 or can be a fragment of at least 20 contiguous nucleotides that are 95-100% identical to SEQ ID NO: 3.

Also described herein, are methods of treating a wound in a subject in need thereof, the method that can include the step of administering an amount of a pharmaceutical formulation as previously described and described elsewhere herein. In some aspects, the amount of the pharmaceutical formulation can be administered topically. In some aspects, the amount of the pharmaceutical formulation can be administered directly to the wound. In some aspects, administration can occur on or more times. In some aspects, the wound can be an ischemic wound.

BRIEF DESCRIPTION OF THE DRAWINGS

FIGS. 2A-2B show micrographic images demonstrating the results of a scratch assay to assess migration of young human dermal fibroblasts exposed to unconditioned medium.

Figure 10A:
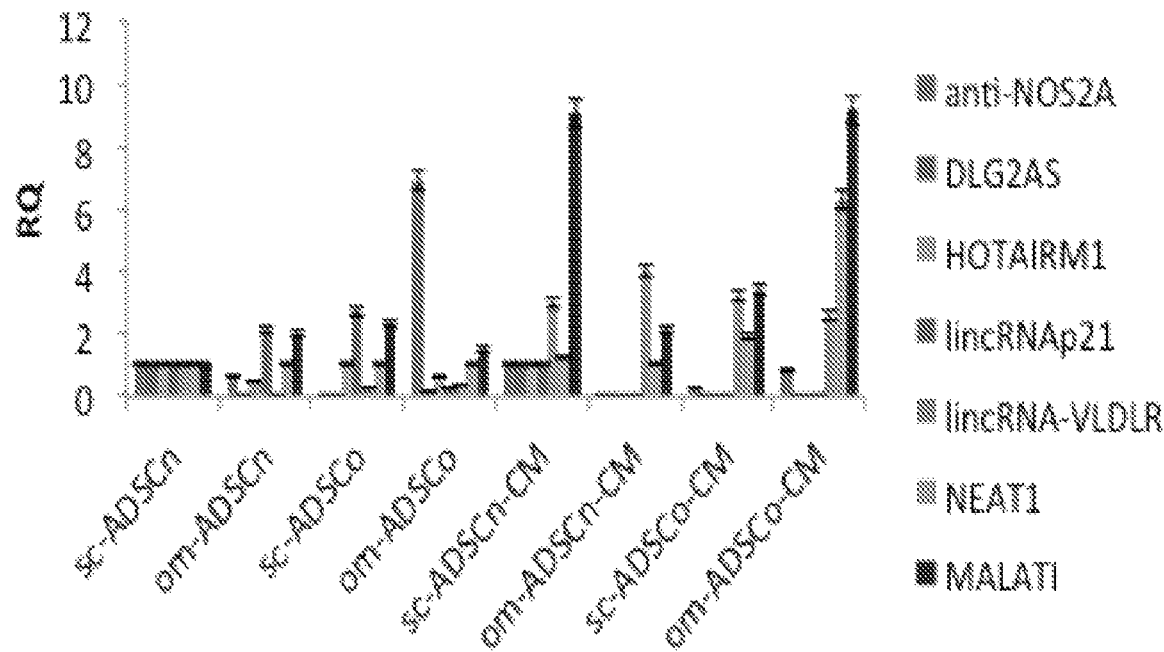
Figure 10B:
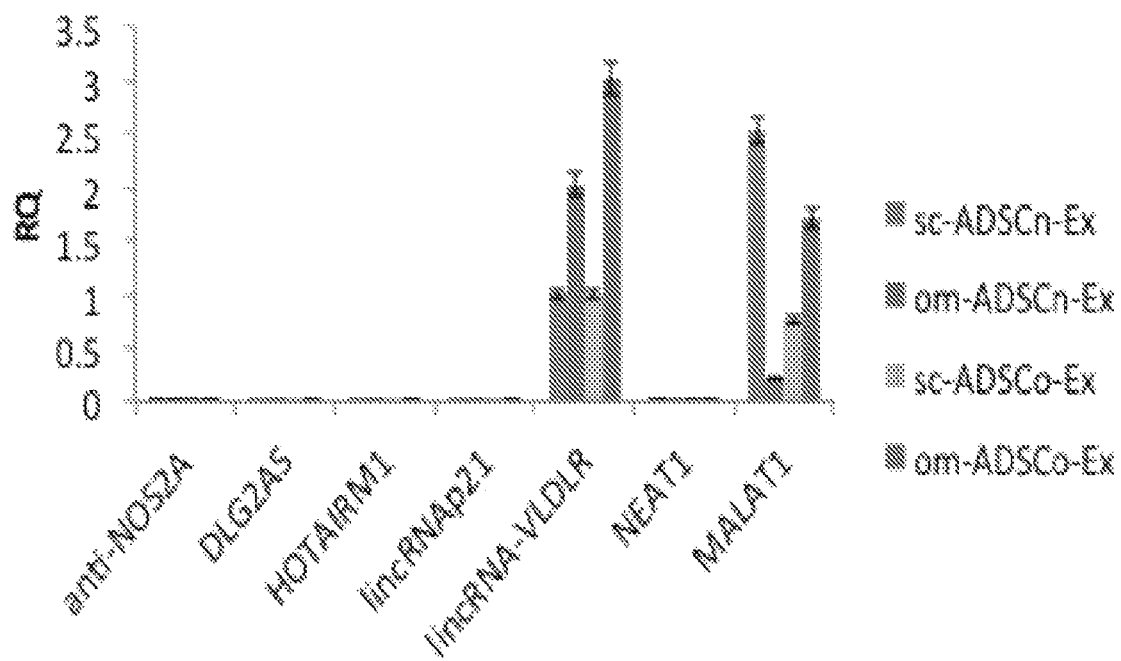

FIGS. 10A-10B show graphs demonstrating the RNA expression profile of several lncRNA and VLDLRs in conditioned medium (CM) and exosomes as detected by qRT-PCR.

Figures 11A, 11B:
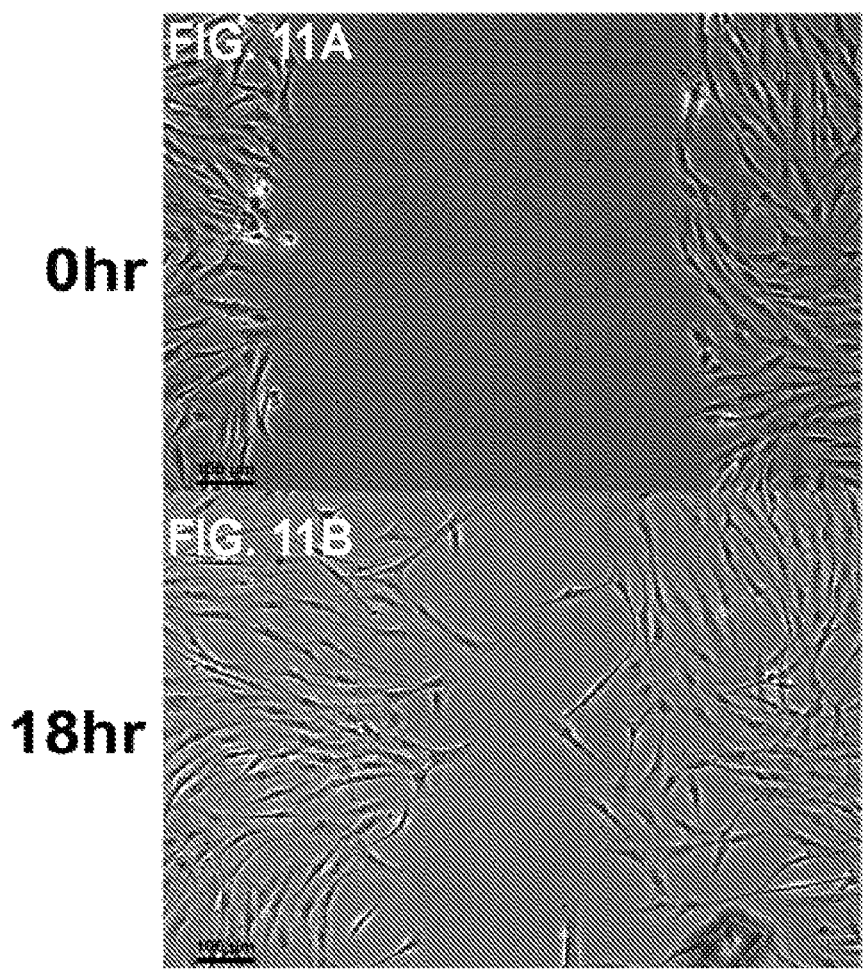

FIGS. 11A-11B show micrographic images of the transfection control cells (FIGS. 11A-11B).

Figure 12:
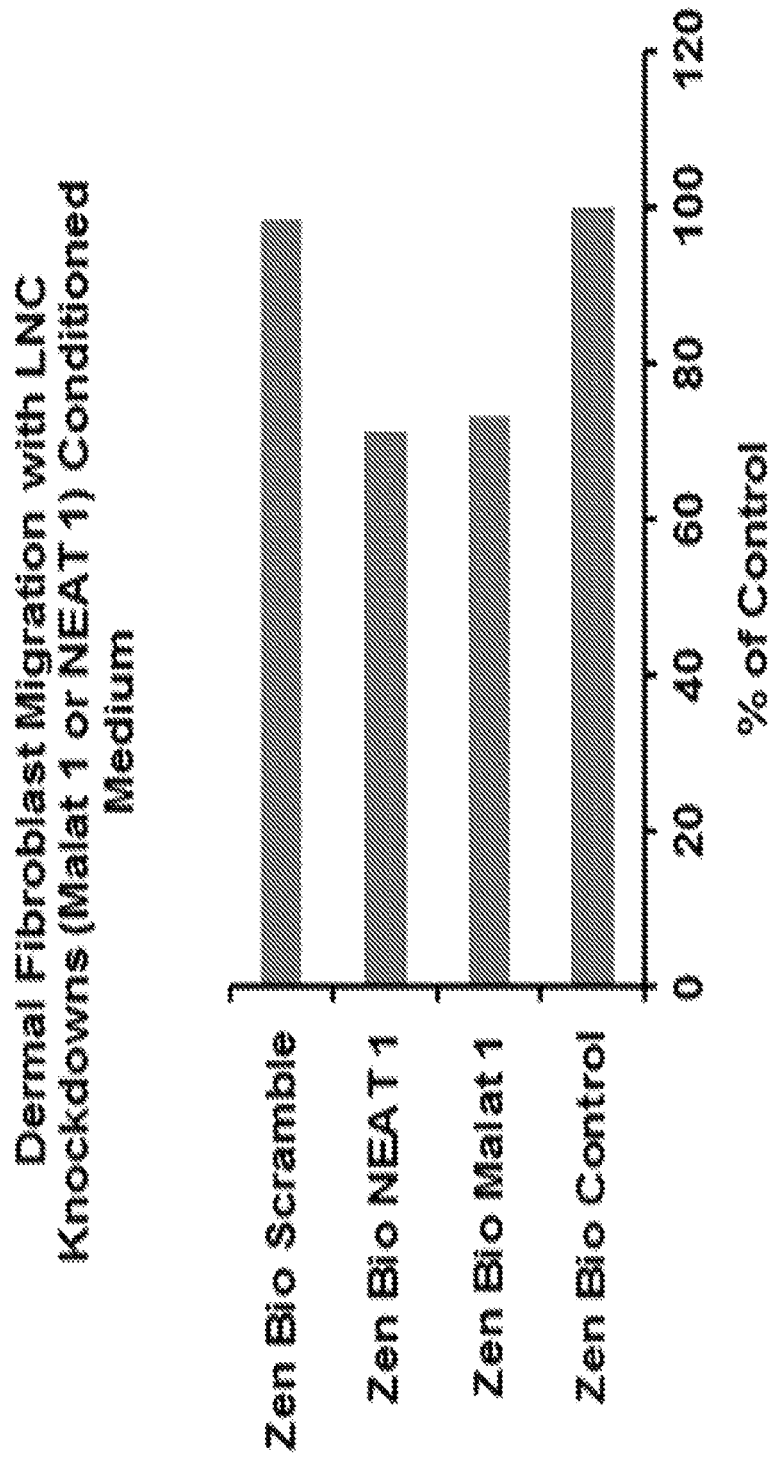
Figures 13A, 13B, 13C, 13D, 13E, 13F:
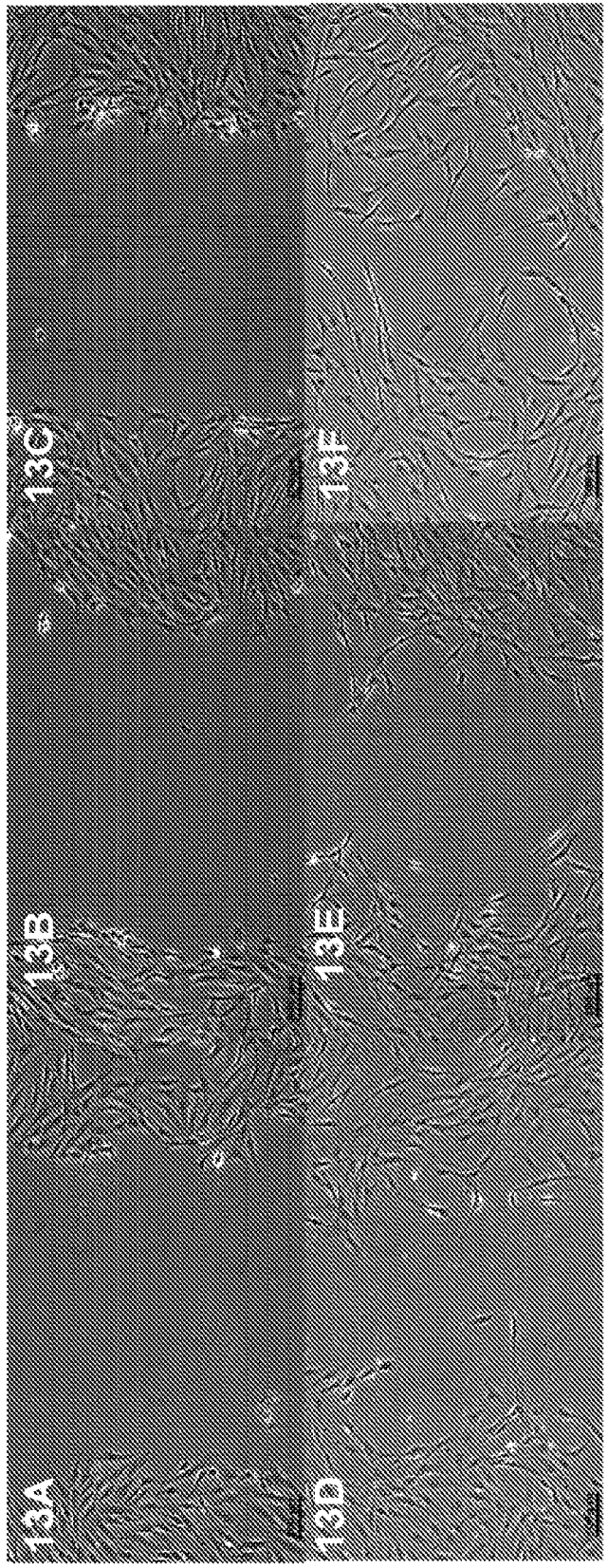

FIG. 12 shows a graph demonstrating the quantitative results from the dermal fibroblast migration tests in Malat 1 and NEAT 1 knockdown in cells cultured in conditioned medium at 18 h as imaged in FIGS. 11A-B and 13B, 13D, and 13F. Results are shown as of control.

FIGS. 13A-13F show micrographic images of fibroblasts having knockdown of MALAT1 or NEAT 1 and the scramble control at 0 and 18 h and the effect of MALAT1 depletion on hADSC CM blocked cell migration. Briefly, young donor human dermal fibroblasts were plated in 6 well dishes and when 95% confluent, cells were scratched (3×) with a 200 μL pipette. Cells were treated with mitomycin C for about 2 hrs. Cell media from MALAT1 antisense oligonucleotide (ASO) treated or "scrambled" ASO treated or ADSC was added (about 2 mL) for about 18 h. After capturing images, migrating cells were counted in a field of the 3 scratch areas.

Figure 14:
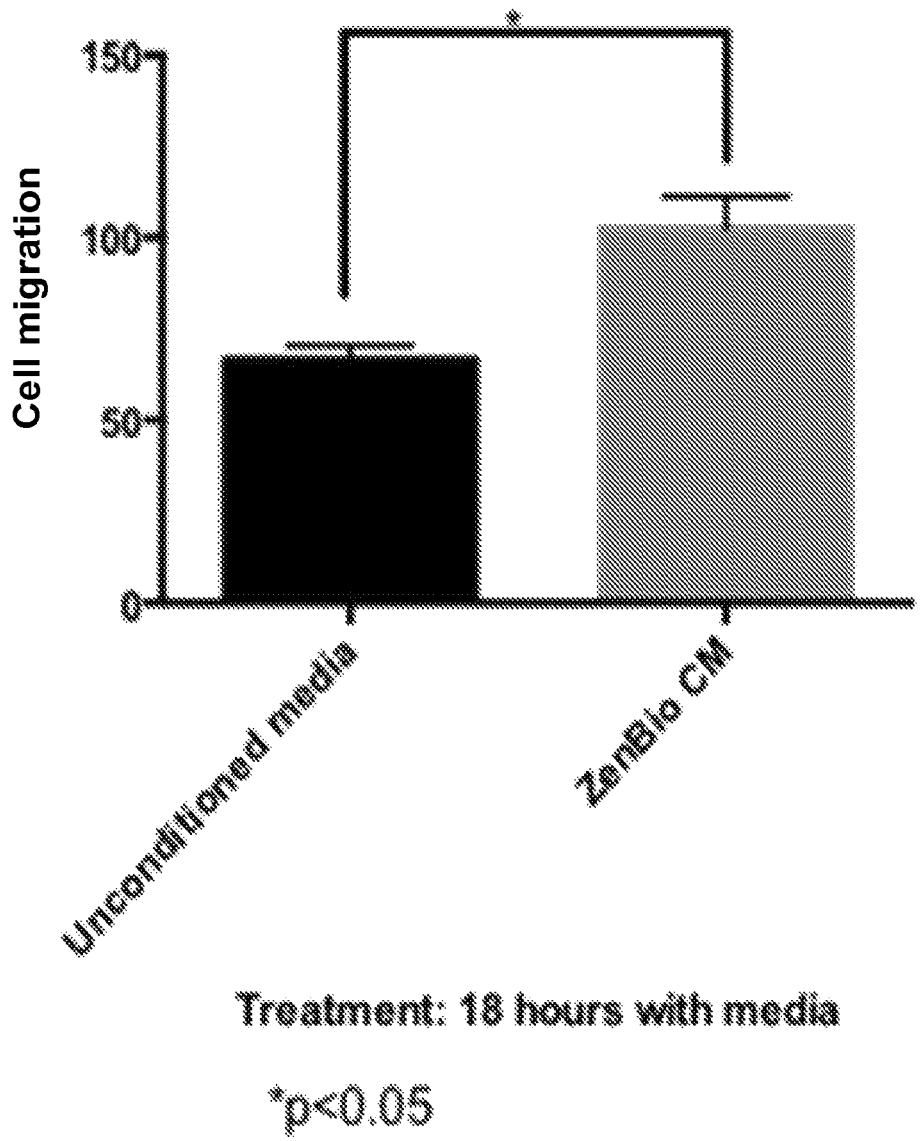

FIG. 14 shows a graph demonstrating the effect of conditioned media from adipose derived stem cells (ADSC) on cell migration in human dermal fibroblasts. Briefly, young donor human dermal fibroblasts (HDF) were plated in 6 well dishes and when about 95% confluent, cells were scratched (3×) with a 200 μL pipette. Cells were treated with mitomycin C for about 2 h. Cell media from ZenBio ADSC was added (about 2 mL) for about 18 h. Unconditioned media (Lonza MSGMCD) was added as the control. After capturing images, migrating cells were counted in a field of the 3 scratch areas. PRISM™ analysis of the data indicated P<0.05.

Figure 15:
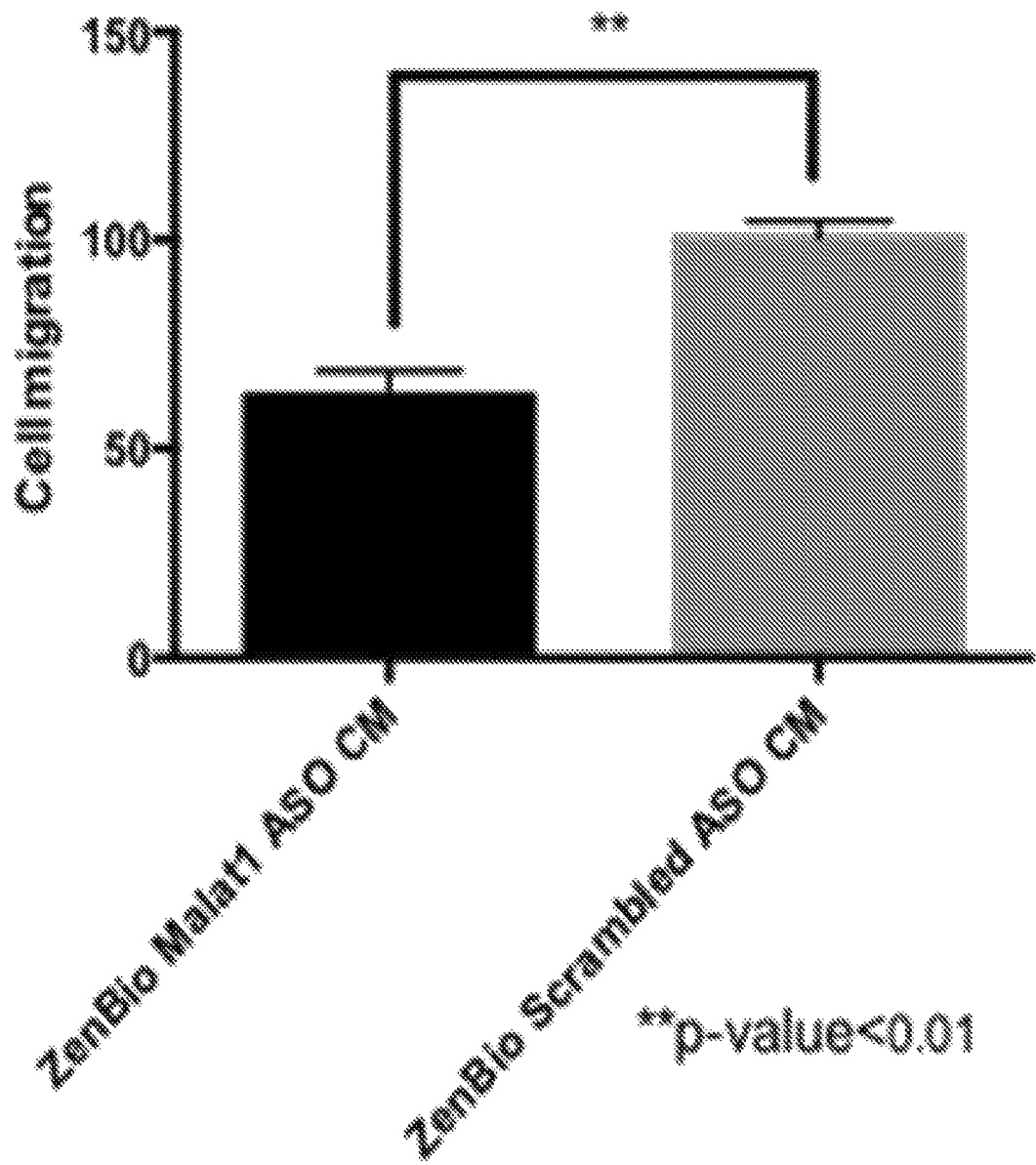

FIG. 15 shows a graph demonstrating the number of cells counted in a field of the 3 scratch areas of FIGS. 13A-13F. After capturing images, migrating cells were counted in a field of the 3 scratch areas. PRISM™ analysis of the data indicated P<0.01.

Figure 16:
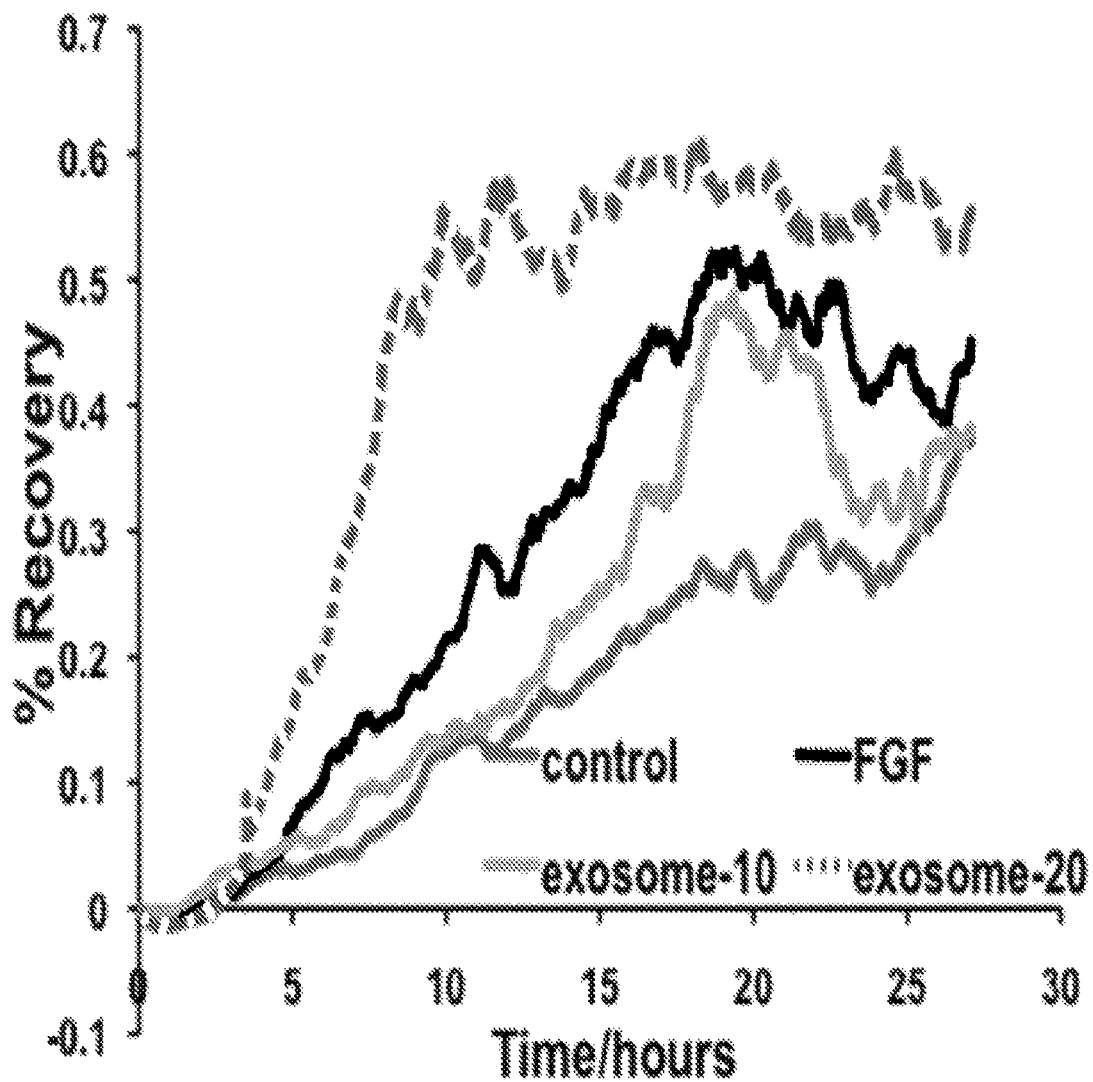

FIG. 16 shows a graph demonstrating the effect of conditioned media from ADSC on HDF cell migration in an ECIS wounding assay. Briefly, HDF cells on the microelectrodes of the ECIS wells were killed with a high electrical voltage. Subsequently, the migration of viable cells onto the wounded microelectrodes was measured in real-time by electrical resistance in the presence of bFGF (about 400 nM), about 10 μg/mL exosomes, and about 20 μg/mL exosome respectively. The percentage of recovery was calculated by the difference in the resistance of each time point and the resistance of the first time point after wounding divided by the resistance before the wounding. The micrographs are representative of three ECIS wells at each time point.

Figure 17:
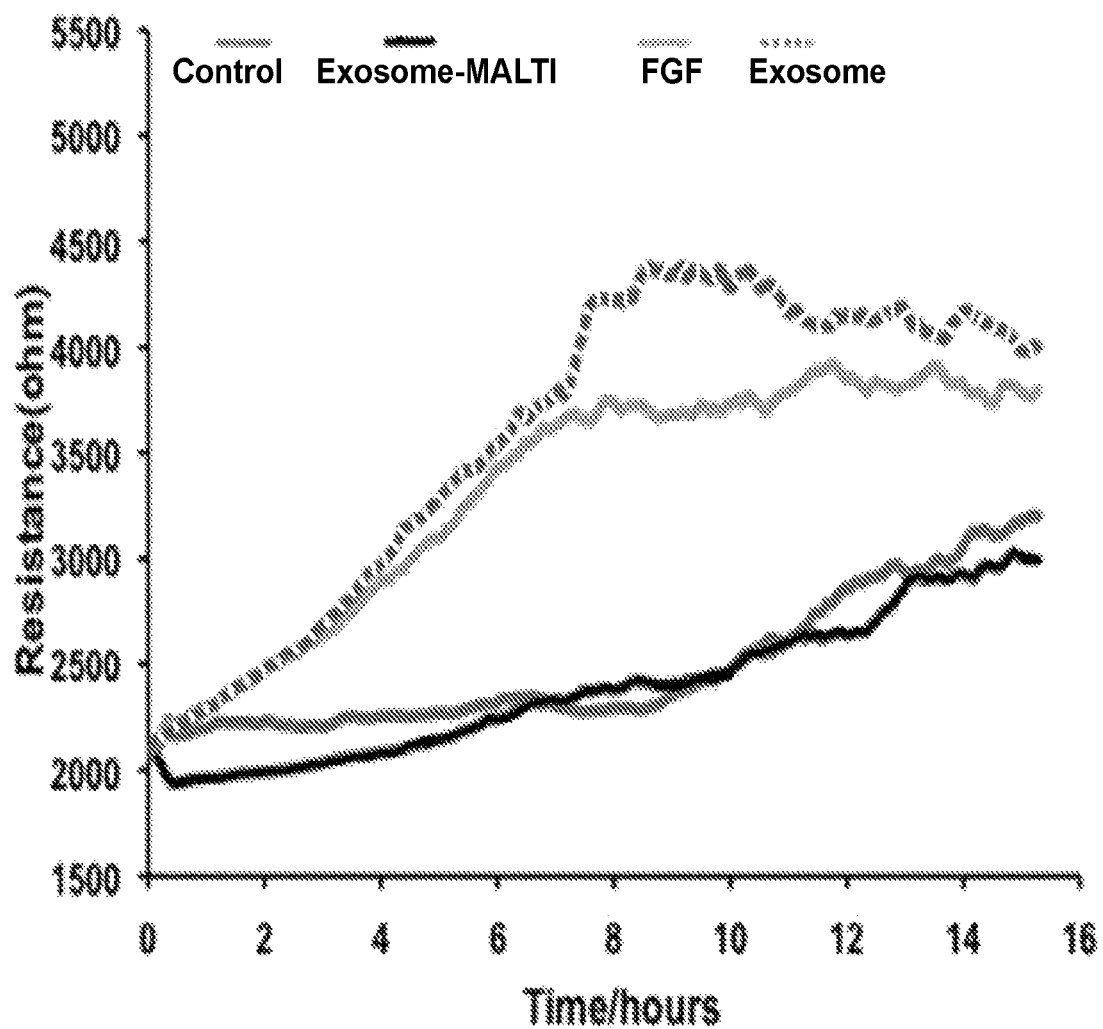

FIG. 17 shows a graph demonstrating the effect of MALAT1 depletion on HDF cell migration as measured by an ECIS wound healing assay. Briefly, HDF cells on the micro-electrodes of the ECIS wells were killed with a high electrical voltage. Subsequently, the migration of viable cells into the wounded microelectrodes was measured in real-time by electrical resistance in the presence of bFGF (about 400 nM), 20 μg/mL exosome, about 20 μg/mL exosome-MALATl respectively. The micrographs are representative of three ECIS wells at each time point.

Figure 18:
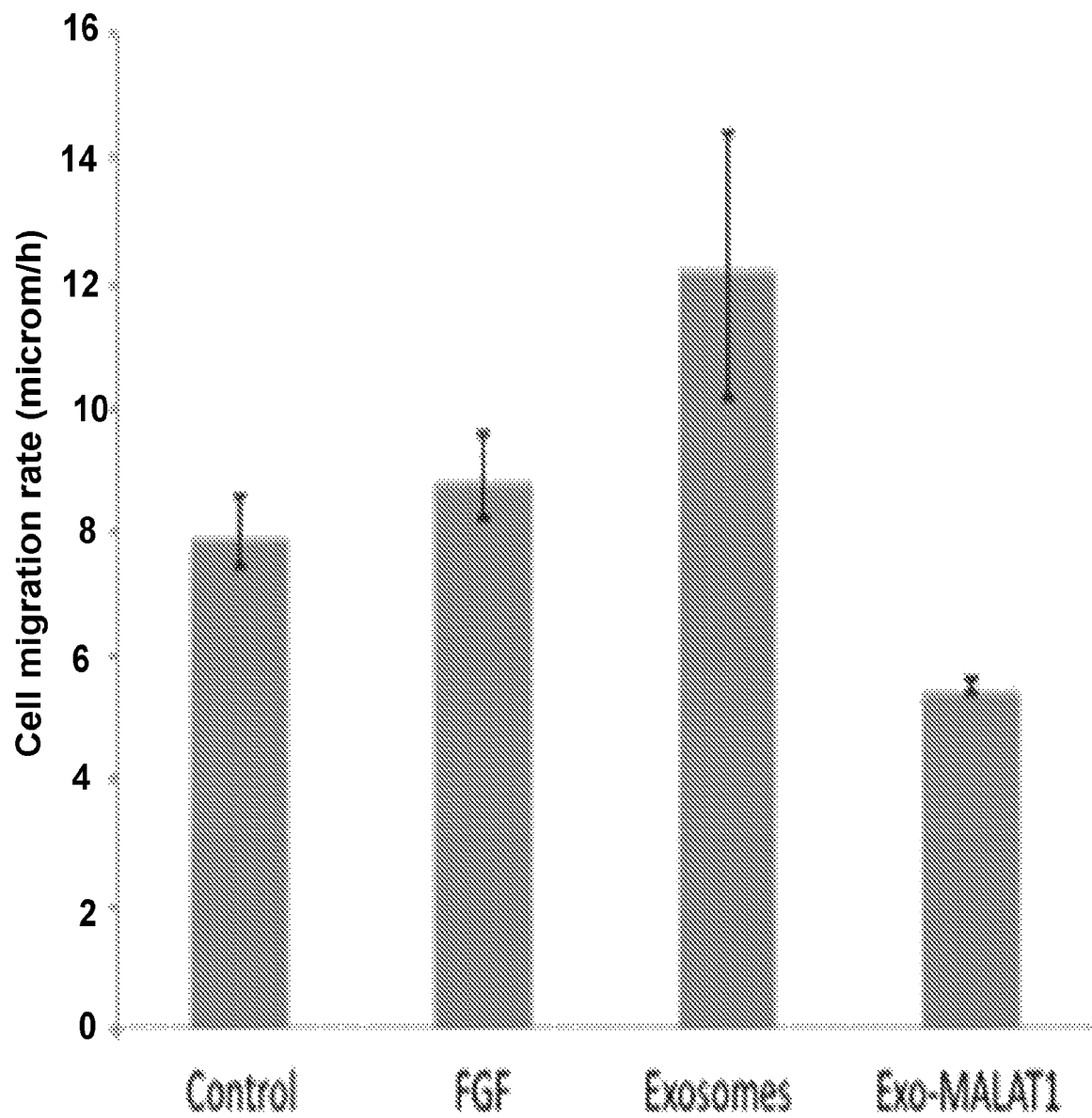

FIG. 18 shows a graph demonstrating the peak responses as cell migration rate from the HDF treatment groups described in relation to FIG. 17.

Further aspects of the present disclosure will be readily appreciated upon review of the detailed description of its various embodiments, described below, when taken in conjunction with the accompanying drawings.

DETAILED DESCRIPTION

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of molecular biology, microbiology, nanotechnology, organic chemistry, biochemistry, botany and the like, which are within the skill of the art. Such techniques are explained fully in the literature.

Definitions

Unless otherwise specified the following definitions can apply herein to the following terms:

As used herein, "about," "approximately," and the like, when used in connection with a numerical variable, generally refers to the value of the variable and to all values of the variable that are within the experimental error (e.g., within the 95% confidence interval for the mean) or within ±10% of the indicated value, whichever is greater.

As used herein, "control" can refer to an alternative subject or sample used in an experiment for comparison purposes and included to minimize or distinguish the effect of variables other than an independent variable.

As used herein, "pharmaceutically acceptable carrier or excipient" can refer to a carrier or excipient that is useful in preparing a pharmaceutical formulation that is generally safe, non-toxic, and is neither biologically or otherwise undesirable, and includes a carrier or excipient that is acceptable for veterinary use as well as human pharmaceutical use. A "pharmaceutically acceptable carrier or excipient" as used in the specification and claims includes both one and more than one such carrier or excipient.

As used herein, "pharmaceutical formulation" can refer to the combination of an active agent, compound, or ingredient with a pharmaceutically acceptable carrier or excipient, making the composition suitable for diagnostic, therapeutic, or preventive use in vitro, in vivo, or ex vivo.

As used interchangeably herein, "subject," "individual," or "patient," refers to a vertebrate, preferably a mammal, more preferably a human. Mammals include, but are not limited to, murines, simians, humans, farm animals, sport animals, and pets. The term "pet" includes a dog, cat, guinea pig, mouse, rat, rabbit, ferret, and the like. The term "farm animal" includes a horse, sheep, goat, chicken, pig, cow, donkey, llama, alpaca, turkey, and the like.

As used herein, "therapeutic" generally can refer to treating, healing, and/or ameliorating a disease, disorder, condition, or side effect, or to decreasing in the rate of advancement of a disease, disorder, condition, or side effect. The term also includes within its scope enhancing normal physiological function, palliative treatment, and partial remediation of a disease, disorder, condition, side effect, or symptom thereof.

As used herein, the terms "treating" and "treatment" can refer generally to obtaining a desired pharmacological and/or physiological effect. The effect may be prophylactic in terms of preventing or partially preventing a disease, symptom or condition thereof.

As used herein, "active agent" or "active ingredient" refers to a component or components of a composition to which the whole or part of the effect of the composition is attributed.

As used herein, "dose," "unit dose," or "dosage" refers to physically discrete units suitable for use in a subject, each unit containing a predetermined quantity of a collagen or fragment thereof, composition, or formulation described herein calculated to produce the desired response or responses in association with its administration.

As used herein, "administering" refers to an administration that is oral, topical, intravenous, subcutaneous, transcutaneous, transdermal, intramuscular, intra-joint, parenteral, intra-arteriole, intradermal, intraventricular, intracranial, intraperitoneal, intralesional, intranasal, rectal, vaginal, by inhalation, or via an implanted reservoir. The term "parenteral" includes subcutaneous, intravenous, intramuscular, intra-articular, intra-synovial, intrasternal, intrathecal, intrahepatic, intralesional, and intracranial injections or infusion techniques.

As used herein, "effective amount" can refer to the amount of a composition described herein or pharmaceutical formulation described herein that will elicit a desired biological or medical response of a tissue, system, animal, plant, protozoan, bacteria, yeast or human that is being sought by the researcher, veterinarian, medical doctor or other clinician. The "effective amount" can be an amount of a composition or compound that can increase rate of wound healing, including ischemic wound healing, increase angiogenesis in a wound (including but not limited to ischemic wounds), and/or increase cell migration, proliferation, and/or differentiation of skin cells. The term "effective amount" can also include "effective concentrations," which are concentrations of composition or compound described herein effective to increase rate of wound healing, including ischemic wound healing, increase angiogenesis in a wound (including but not limited to ischemic wounds), and/or increase cell migration, proliferation, and/or differentiation of skin cells.

As used herein, "anti-infective" refers to compounds or molecules that can either kill an infectious agent or inhibit it from spreading. Anti-infectives include, but are not limited to, antibiotics, antibacterials, antifungals, antivirals, and antiprotozoals.

As used herein, "aptamer" refers to single-stranded DNA or RNA molecules that can bind to pre-selected targets including proteins with high affinity and specificity. Their specificity and characteristics are not directly determined by their primary sequence, but instead by their tertiary structure.

As used herein, "concentrated" refers to a molecule, including but not limited to a polynucleotide, peptide, polypeptide, protein, antibody, or fragments thereof, that is distinguishable from its naturally occurring counterpart in that the concentration or number of molecules per volume is greater than that of its naturally occurring counterpart.

As used herein, "chemotherapeutic agent" or "chemotherapeutic" refer to a therapeutic agent utilized to prevent or treat cancer.

As used herein, "diluted" refers to a molecule, including but not limited to a polynucleotide, peptide, polypeptide, protein, antibody, or fragments thereof, that is distinguishable from its naturally occurring counterpart in that the concentration or number of molecules per volume is less than that of its naturally occurring counterpart.

As used herein, "identity," is a relationship between two or more polypeptide sequences, as determined by comparing the sequences. In the art, "identity" also refers to the degree of sequence relatedness between polypeptide as determined by the match between strings of such sequences. "Identity" can be readily calculated by known methods, including, but not limited to, those described in (Computational Molecular Biology, Lesk, A. M., Ed., Oxford University Press, New York, 1988; Biocomputing: Informatics and Genome Projects, Smith, D. W., Ed., Academic Press, New York, 1993; Computer Analysis of Sequence Data, Part I, Griffin, A. M., and Griffin, H. G., Eds., Humana Press, New Jersey, 1994; Sequence Analysis in Molecular Biology, von Heinje, G., Academic Press, 1987; and Sequence Analysis Primer, Gribskov, M. and Devereux, J., Eds., M Stockton Press, New York, 1991; and Carillo, H., and Lipman, D., SIAM J. Applied Math. 1988, 48: 1073. Preferred methods to determine identity are designed to give the largest match between the sequences tested. Methods to determine identity are codified in publicly available computer programs. The percent identity between two sequences can be determined by using analysis software (e.g., Sequence Analysis Software Package of the Genetics Computer Group, Madison Wis.) that incorporates the Needelman and Wunsch, (J. Mol. Biol., 1970, 48: 443-453) algorithm (e.g., NBLAST, and XBLAST). The default parameters are used to determine the identity for the polypeptides of the present disclosure.

As used herein, "immunomodulator," refers to an agent, such as a therapeutic agent, which is capable of modulating or regulating one or more immune function or response.

As used herein, "isolated" means separated from constituents, cellular and otherwise, in which the polynucleotide, peptide, polypeptide, protein, antibody, or fragments thereof, are normally associated with in nature. A non-naturally occurring polynucleotide, peptide, polypeptide, protein, antibody, or fragments thereof, do not require "isolation" to distinguish it from its naturally occurring counterpart.

The term "molecular weight", as used herein, generally refers to the mass or average mass of a material. If a polymer or oligomer, the molecular weight can refer to the relative average chain length or relative chain mass of the bulk polymer. In practice, the molecular weight of polymers and oligomers can be estimated or characterized in various ways including gel permeation chromatography (GPC) or capillary viscometry. GPC molecular weights are reported as the weight-average molecular weight ($M_w$) as opposed to the number-average molecular weight ($M_n$). Capillary viscometry provides estimates of molecular weight as the inherent viscosity determined from a dilute polymer solution using a particular set of concentration, temperature, and solvent conditions.

As used herein, "negative control" refers to a "control" that is designed to produce no effect or result, provided that all reagents are functioning properly and that the experiment is properly conducted. Other terms that are interchangeable with "negative control" include "sham," "placebo," and "mock."

As used herein, "patient" refers to an organism, host, or subject in need of treatment.

As used herein, "positive control" refers to a "control" that is designed to produce the desired result, provided that all reagents are functioning properly and that the experiment is properly conducted.

As used herein, "expression" refers to the process by which polynucleotides are transcribed into RNA transcripts. In the context of mRNA and other translated RNA species, "expression" also refers to the process or processes by which the transcribed RNA is subsequently translated into peptides, polypeptides, or proteins.

As used herein, "gene" refers to a hereditary unit corresponding to a sequence of DNA that occupies a specific location on a chromosome and that contains the genetic instruction for a characteristic(s) or trait(s) in an organism. "Gene" also refers to the specific sequence of DNA that is transcribed into an RNA transcript that can be translated into a polypeptide or be a catalytic or non-translated RNA molecule including but not limited to tRNA, siRNA, piRNA, miRNA, lncRNA, and shRNA.

As used herein, "long non-coding RNA" refers to non-coding RNA molecules containing about 200 or more nucleotides that are not translated to a protein.

As used herein, "paralog" can refer to a homologue produced via gene duplication of a gene. In other words, paralogs are homologues that result from divergent evolution from a common ancestral gene. A "functional paralog" can refer to a paralog that has a similar function or action.

As used herein, "orthologues" can refer to homologues produced by speciation followed by divergence of sequence but not activity in separate species. When speciation follows duplication and one homologue sorts with one species and the other copy sorts with the other species, subsequent divergence of the duplicated sequence is associated with one or the other species. Such species specific homologues are referred to herein as orthologues. A "functional orthologue" can refer to a orthologue that has a similar function or action.

As used herein, "homologue" can refer to a polypeptide (or polynucleotide) sequence that shares a threshold level (set forth elsewhere herein) of similarity and/or identity as determined by alignment of matching amino acids (or nucleic acids). Two or more polypeptides determined to be homologues are said to be homologues. Homology is a qualitative term that describes the relationship between polypeptide sequences that is based upon the quantitative similarity. A "functional homologue" can refer to a homologue that has a similar function or action.

As used herein, "conditioned media" can refer to cell culture media containing biologically active components released by, excreted by, secreted by, or otherwise obtained from cells and/or tissues that were previously cultured in the cell culture media.

Discussion

Chronically ill patents are faced with challenges, particularly when they develop recalcitrant wounds. A number of local and systemic factors impact wound healing include, but not limited to, oxygenation, infection, age, sex hormones, stress, diabetes, obesity, medications (e.g. chemotherapy), alcoholism, smoking and nutrition. The wound healing process incudes four integrated and overlapping phases: (1) homeostasis, (2) inflammation, (3) proliferation, and (4) tissue remodeling. These phases must occur rapidly and appropriately in the proper sequence and continue for a specific duration for wound healing to occur successfully. Investigations and clinical studies have provided a wealth of information about normal and impaired wound healing. In sum, oxygen levels are important for optimum wound healing. Hypoxia (low oxygen) stimulates the release of growth factors and angiogenesis, while oxygen is needed to sustain the process. Inflammation, a normal part of wound healing is important in the removal of microorganisms. In complete removal of bacteria and endotoxins can lead to infections at the injured skin surface, lengthening the inflammatory phase. Prolongation and escalation of the inflammatory phase contributes to a failure to heal. It also leads to increased levels of matrix metalloproteinases that can degrade the extracellular matrix. Systemic factors also contribute to impaired wound healing.

The needs of a healing wound are complex. Single and multiple factors play a role in the individual features to contribute to the overall outcome. Mesenchymal stem cells (MSC) derived from bone marrow can improve wound fibroblast migration in vitro. Co-cultured MSCs with fibroblasts in Boyden chambers that fibroblasts migrated toward MSCs in the chamber. To obtain bone marrow stem cells, invasive and painful techniques are required. As such, there still exists a need for non-bone marrow based wound healing techniques and compositions.

With the foregoing in mind, described herein are compositions and formulations containing exosomes secreted by adipose derived stem cells (ADSC) and/or one or more biologic factors contained within an adipose stem cell derived exosome. In some embodiments, the biologic factor can be a long coding RNA, such as MALAT1, linc-VLDLR, and/or GAS5. Also provided herein are methods of treating a wound that can include the step of administering an amount of a composition or formulation containing exosomes secreted by adipose derived stem cells and/or one or more biologic factors contained within an adipose stem cell derived exosome. The exosomes and other formulations provided herein can provide faster and/or more efficient wound healing than current techniques. Other compositions, compounds, methods, features, and advantages of the present disclosure will be or become apparent to one having ordinary skill in the art upon examination of the following drawings, detailed description, and examples. It is intended that all such additional compositions, compounds, methods, features, and advantages be included within this description, and be within the scope of the present disclosure.

Exosomes and Exosomal lncRNAs

Figure 1:
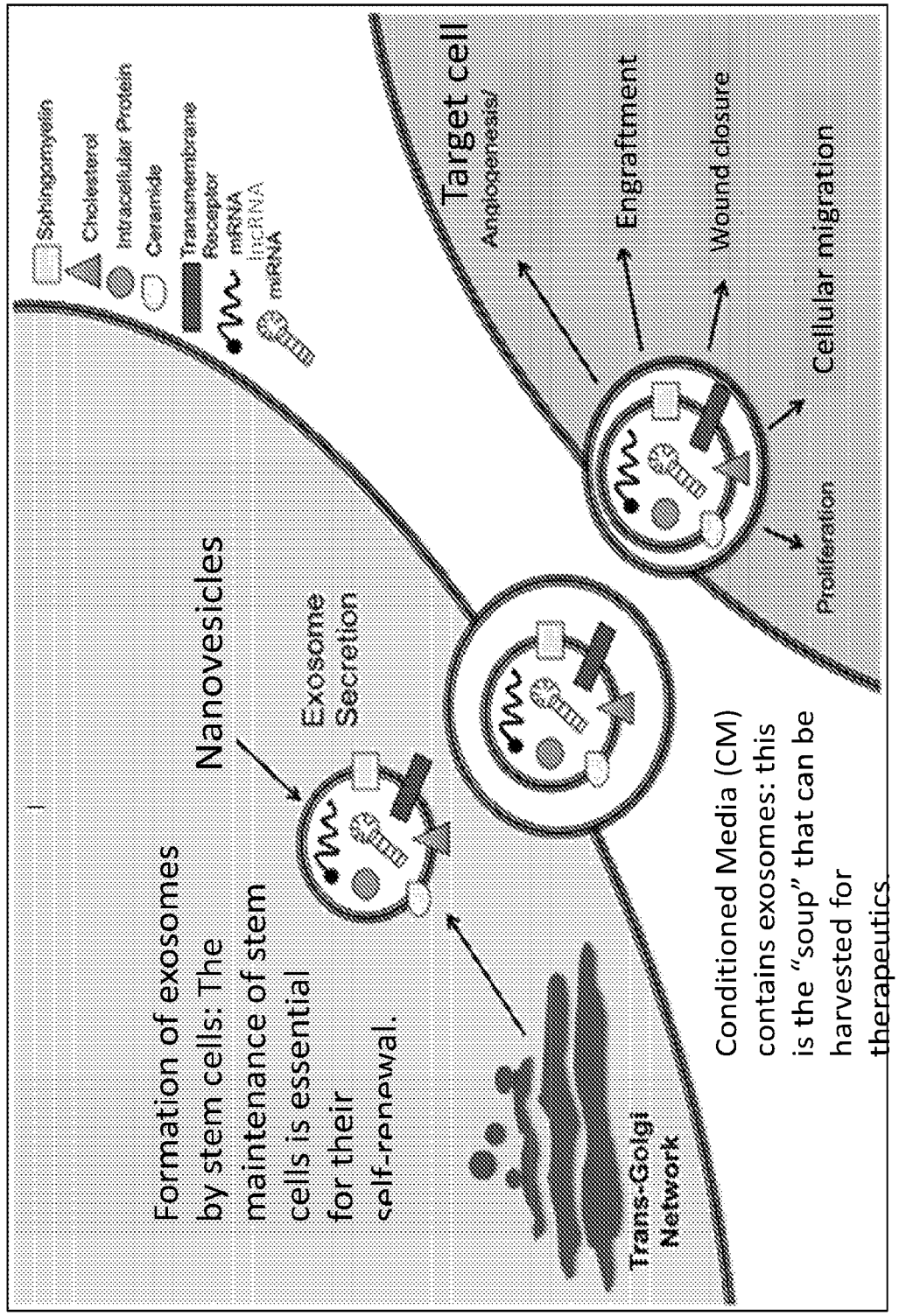
FIG. 1 shows a diagram of stem cells secreting factors that can assist patient's wounded cells.

As shown in FIG. 1, adipose derived stem cells can produce and secrete exosomes. Provided herein are condition media containing adipose stem cell derived exosomes, adipose stem cell derived exosomes, and formulations thereof that can be effective for and used in the treatment of wounds. In embodiments, the wounds are recalcitrant wounds, such as ischemic wounds. In some embodiments, conditioned media can contain exosomes produced by adipose derived stem cells. In some embodiments, the exosomes can be purified and/or concentrated from the conditioned media. The exosomes, whether or not purified from the conditioned media, can contain one or more lncRNAs, including, but not limited to, MALAT1, linc-VLDR, GAS5, and/or functional homologues, paralogs, and/or orthologues thereof. In some embodiments, the most abundant lncRNA in one or more exosomes secreted by the adipose stem cells can be MALAT1. Techniques of determining the expression of lncRNAs, including MALAT1, are generally known in the art. The exosomes can be formed by isolating and culturing adipose derived stem cells for a period of time and collecting the formed exosomes secreted by the adipose derived stem cells by obtaining the culture medium and optionally purifying the exosomes from the culture medium. In some embodiments, the adipose derived stem cells are adipose derived mesenchymal stem cells. The period of time for culturing the adipose derived stem cells and collecting the exosomes can range from about 24 to 48 hours In some embodiments, the culture medium can be replaced with serum-free mesenchymal stem cell basal medium. As a non-limiting example, the serum-free mesenchymal stem cell basal medium can be MSC-BM-CD from Lonza Cat. No. #00190620). Other suitable media will be appreciated by those of ordinary skill in the art.

In addition to the techniques provided herein, the adipose derived stem cells, including adipose mesenchymal stem cells, can be obtained using techniques generally known in the art. In some embodiments, the adipose tissue can be collected by a suitable method (aspiration and/or liposuction) and the stromal vascular fraction of the adipose tissue can be isolated. Various techniques for obtaining the stromal vascular fraction and collection the stems cells within will be instantly appreciated by one of ordinary skill in the art. See e.g. Mailey, B. et al., 2014. Methods. Mol. Biol. 1210: 161-181. In addition to the techniques provided herein, the adipose derived stem cells can be cultured using techniques generally known in the art.

As previously described, the exosomes can include an amount of MALAT1 lncRNA or other lncRNAs. The exosomes can contain one or more lncRNAs, including, but not limited to, MALAT 1, linc-VLDR, GAS5 and/or functional homologues, orthologues, or paralogues thereof. In some embodiments, the MALAT 1 lncRNA is the most abundant lncRNA in the exosomes. In some embodiments, the lncRNA can have a sequence about 95% to 100% identical to any one of SEQ ID NOs: 1-3 or a fragment of at least 20 contiguous nucleotides thereof. In some embodiments, the MALAT1, VLDLR, and/or GAS5 lncRNA can be isolated from the exosomes of adipose derived stem cells or de novo chemically synthesized and thus separated from the other components it associates with in nature.

The average size of the exosomes can range from 80 nm, to about 120 nm in diameter. The average hydrodynamic size of the exosomes can range from about 80 nm, to about 120 nm. The diameter or size of the exosomes can be measured, for example, by filtration via a membrane with a relevant size cutoff, electron microscopy, or SDS-PAGE or other biological assay. Hydrodynamic radius can be measured, for example, by laser diffraction or dynamic light scattering. Exosomes can fuse together and become larger, also, they can divide. Conditions governing the exact size of exosomes are currently unknown. Exosomes referred to in this application are identified not only by approximate size, but their expression of CD9, 63 and 81 by western blot.

Formulations Containing ADSC Exosomes and/or MALAT1 lncRNA

Also described herein are formulations, including pharmaceutical formulations, which can contain an amount of the conditioned media, exosomes and/or an amount of purified MALAT1, VLDLR, or GAS5 lncRNA described elsewhere herein. In some embodiments, the pharmaceutical formulation is the conditioned media containing the exosomes. The amount of the conditioned media, exosomes and/or an amount of purified MALAT1, VLDLR, or GAS5 lncRNA can be an effective amount. The amount of the conditioned media, exosomes and/or an amount of purified MALAT1, VLDLR, or GAS5 lncRNA can be effective to stimulate would healing and/or increase the rate of wound healing, including but not limited to increasing ischemic wound healing or rate thereof.

Formulations, including pharmaceutical formulations can be formulated for delivery via a variety of routes, including but not limited to topical, subcutaneously, and/or intravenously, and can contain a pharmaceutically acceptable carrier. Techniques and formulations generally can be found in *Remmington's Pharmaceutical Sciences*, Meade Publishing Co., Easton, Pa. (20$^{th}$ Ed., 2000), the entire disclosure of which is herein incorporated by reference. For systemic administration, an injection is useful, including intramuscular, intravenous, intraperitoneal, and subcutaneous, transdermal, and topical. For injection, the therapeutic compositions of the invention can be formulated in liquid solutions, for example in physiologically compatible buffers such as Hank's solution or Ringer's solution. In addition, the exosomes can be formulated in solid form (e.g. lyophilized) and redissolved or suspended immediately prior to use. Formulations, including pharmaceutical formulations, of the exosomes can be characterized as being at least sterile and pyrogen-free. These formulations include formulations for human and veterinary use.

The pharmaceutical formulations can include a pharmaceutically acceptable carrier. Suitable pharmaceutically acceptable carriers include, but are not limited to water, salt solutions, alcohols, gum arabic, vegetable oils, benzyl alcohols, polyethylene glycols, gelatin, carbohydrates such as lactose, amylose or starch, magnesium stearate, talc, silicic acid, viscous paraffin, perfume oil, fatty acid esters, hydroxyl methylcellulose, and polyvinyl pyrrolidone, which do not deleteriously react with exosomes and/or an amount of purified MALAT1, VLDLR, or GAS5 lncRNA. In some embodiments, the pharmaceutically acceptable carrier can be the cell culture medium that the adipose derived stem cells are cultured in (the conditioned media). Thus, in these embodiments, the conditioned media is the pharmaceutical formulation.

The pharmaceutical formulations can be sterilized, and if desired, mixed with auxiliary agents, such as platelet rich plasma, preservatives, stabilizers, wetting agents, emulsifiers, salts for influencing osmotic pressure, buffers, and the like which do not deleteriously react with the exosomes and/or an amount of purified MALAT1, VLDLR or GAS5 lncRNA.

A pharmaceutical formulation can be formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerin, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic, and stored at −80° C.

Formulations, including pharmaceutical formulations, suitable for injectable use can include sterile aqueous solutions (where water soluble) or dispersions and sterile powders for the extemporaneous preparation of sterile injectable solutions or dispersions. For intravenous administration, suitable carriers can include physiological saline, bacteriostatic water, Cremophor EM™ (BASF, Parsippany, N.J.) or phosphate buffered saline (PBS). Injectable pharmaceutical formulations can be sterile and can be fluid to the extent that easy syringability exists. Injectable pharmaceutical formulations can be stable under the conditions of manufacture and storage and must be preserved against the contaminating action of microorganisms such as bacteria and fungi. The carrier can be a solvent or dispersion medium containing, for example, water, ethanol, a pharmaceutically acceptable polyol like glycerol, propylene glycol, liquid polyethylene glycol, and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In some embodiments, it can be useful to include isotonic agents, for example, sugars, polyalcohols such as mannitol, sorbitol, and sodium chloride in the composition.

Sterile injectable solutions can be prepared by incorporating any of the exosomes and/or an amount of purified lncRNAs described herein in an amount in an appropriate solvent with one or a combination of ingredients enumerated herein, as required, followed by filtered sterilization. Generally, dispersions can be prepared by incorporating exosomes and/or an amount of purified lncRNA into a sterile vehicle which contains a basic dispersion medium and the required other ingredients from those enumerated herein. In the case of sterile powders for the preparation of sterile injectable solutions, examples of useful preparation methods are vacuum drying and freeze-drying which yields a powder of the active ingredient plus any additional desired ingredient from a previously sterile-filtered solution thereof. Systemic administration can also be by transmucosal or transdermal means. For transmucosal or transdermal administration, penetrants appropriate to the barrier to be permeated can be used in the formulation, if needed. In some embodiments, an open wound is being treated and thus the penetrant is optional as application directly to the wound can provide sufficient contact with the wound to promote healing. Suitable penetrants are generally known in the art, and include, for example, for transmucosal administration, detergents, bile salts, and fluidic acid derivatives. Transmucosal administration can be accomplished through the use of nasal sprays or suppositories. For transdermal administration, the exosomes can be formulated into ointments, salves, gels, or creams as generally known in the art. In some embodiments, the exosomes and/or an amount of purified Malat1 lncRNA can be applied via transdermal delivery systems, which can slowly release the exosomes and/or an amount of purified Malat1 lncRNA for percutaneous absorption. Permeation enhancers can be used to facilitate transdermal penetration of the active factors in the conditioned media, if present in the formulation, and/or exosomes. Transdermal patches are described in for example, U.S. Pat. Nos. 5,407,713; 5,352,456; 5,332,213; 5,336,168; 5,290,561; 5,254,346; 5,164,189; 5,163,899; 5,088,977; 5,087,240; 5,008,110; and U.S. Pat. No. 4,921,475

For parenteral administration (i.e., administration through a route other than the alimentary canal), the formulations described herein can be combined with a sterile aqueous solution that is isotonic with the blood of the subject. Such a formulation can be prepared by dissolving the active ingredient (e.g. the exosomes and/or an amount of purified lncRNA) in water containing physiologically-compatible substances, such as sodium chloride, glycine and the like, and having a buffered pH compatible with physiological conditions, so as to produce an aqueous solution, then rendering the solution sterile. The formulation can be presented in unit or multi-dose containers, such as sealed ampoules or vials. The formulation can be delivered by injection, infusion, or other means known in the art.

For transdermal administration, the formulations described herein can be combined with skin penetration enhancers, such as propylene glycol, polyethylene glycol, isopropanol, ethanol, oleic acid, N-methylpyrrolidone and the like, which increase the permeability of the skin to the nucleic acid vectors of the invention and permit the nucleic acid vectors to penetrate through the skin and into the bloodstream. The formulations and/or compositions described herein can be further combined with a polymeric substance, such as ethylcellulose, hydroxypropyl cellulose, ethylene/vinyl acetate, polyvinyl pyrrolidone, and the like, to provide the composition in gel form, which can be dissolved in a solvent, such as methylene chloride, evaporated to the desired viscosity and then applied to backing material to provide a patch.

Dosage Forms

The exosomes, purified lncRNA, and formulations thereof described herein can be provided in unit dose form such as a tablet, capsule, single-dose injection, application or infusion vial, or as a predetermined dose in formulations described above. Where appropriate, the dosage forms described herein can be microencapsulated. The dosage form can also be prepared to prolong or sustain the release of any ingredient.

Effective Amounts

The formulations can contain an effective amount of the exosomes and/or an amount of purified lncRNA (effective for stimulating and/or increasing the rate of wound healing) described herein. In some embodiments, the effective amount of the exosomes and/or an amount of purified MALAT1, VLDLR, or GAS5 lncRNA ranges from about 0.001 pg to about 500 μg or more of the exosomes and/or an amount of purified MALAT1 lncRNA described herein. In some embodiments, the effective amount of the conditioned media, exosomes and/or an amount of purified MALAT1, VLDLR, or GAS5 lncRNA can be about 20 μg/mL. In some embodiments, the effective amount of the exosomes and/or an amount of purified MALAT1 lncRNA described herein can range from about 0.001 pg, 0.01 pg, 0.1 pg, 0.001 μg, 0.01 μg, 0.1 μg, 1 μg, 2 μg, 3 μg, 4 μg, 5 μg, 6 μg, 7 μg, 8 μg, 9 μg, 10 μg, 15 μg, 20 μg, 25 μg, 30 μg, 35 μg, 40 μg, 45 μg, 50 μg, 55 μg, 60 μg, 65 μg, 70 μg, 75 μg, 80 μg, 85 μg, 90 μg, 95 μg, 100 μg, 125 μg, 150 μg, 175 μg, 200 μg, 225 μg, 250 μg, 275 μg, 300 μg, 350 μg, 400 μg, 450 μg to about 500 μg or more or from about 0.01 pg/mL, 0.1, pg/mL, 1 μg/mL, 2 μg/mL, 3 μg/mL, 4 μg/mL, 5 μg/mL, 6 μg/mL, 7 μg/mL, 8 μg/mL, 9 μg/mL, 10 μg/mL, 15 μg/mL, 20 μg/mL, 25 μg/mL, 30 μg/mL, 35 μg/mL, 40 μg/mL, 45 μg/mL, 50 μg/mL, 55 μg/mL, 60 μg/mL, 65 μg/mL, 70 μg/mL, 75 μg/mL, 80 μg/mL, 85 μg/mL, 90 μg/mL, 95 μg/mL, 100 μg/mL, 125 μg/mL, 150 μg/mL, 175 μg/mL, 200 μg/mL, 225 μg/mL, 250 μg/mL, 275 μg/mL, 300 μg/mL, 350 μg/mL, 400 μg/mL, 450 μg/mL to about 500 μg/mL. In some embodiments the effective amount can range from about 9 μg/mL to about 20 μg/mL. In some embodiments the effective amount can range from about 9 μg/mL. In some embodiments the effective amount can range from about 18 μg/mL. In some embodiments the effective amount can range from about 20 μg/mL.

In some embodiments, the effective amount of the exosomes and/or an amount of purified MALAT1 lncRNA described herein can range from about 0.001 pg, 0.01 pg, 0.1 pg, 0.001 μg, 0.01 μg, 0.1 μg, 1 μg, 2 μg, 3 μg, 4 μg, 5 μg, 6 μg, 7 μg, 8 μg, 9 μg, 10 μg, 15 μg, 20 μg, 25 μg, 30 μg, 35 μg, 40 μg, 45 μg, 50 μg, 55 μg, 60 μg, 65 μg, 70 μg, 75 μg, 80 μg, 85 μg, 90 μg, 95 μg, 100 μg, 125 μg, 150 μg, 175 μg, 200 μg, 225 μg, 250 μg, 275 μg, 300 μg, 350 μg, 400 μg, 450 μg to about 500 μg or more or from about 0.01 pg/mL, 0.1, pg/mL, 1 μg/mL, 2 μg/mL, 3 μg/mL, 4 μg/mL, 5 μg/mL, 6 μg/mL, 7 μg/mL, 8 μg/mL, 9 μg/mL, 10 μg/mL, 15 μg/mL, 20 μg/mL, 25 μg/mL, 30 μg/mL, 35 μg/mL, 40 μg/mL, 45 μg/mL, 50 μg/mL, 55 μg/mL, 60 μg/mL, 65 μg/mL, 70 μg/mL, 75 μg/mL, 80 μg/mL, 85 μg/mL, 90 μg/mL, 95 μg/mL, 100 μg/mL, 125 μg/mL, 150 μg/mL, 175 μg/mL, 200 μg/mL, 225 μg/mL, 250 μg/mL, 275 μg/mL, 300 μg/mL, 350 μg/mL, 400 μg/mL, 450 μg/mL to about 500 μg/mL per cm$^2$ of wound area. In some embodiments the effective amount can range from about 9 μg/mL to about 20 μg/mL per cm$^2$ of wound area. In some embodiments the effective amount can range from about 9 μg/mL per cm$^2$ of wound area. In some embodiments the effective amount can range from about 18 μg/mL per cm$^2$ of wound area. In some embodiments the effective amount can range from about 20 μg/mL per cm$^2$ of wound area. In some embodiments the effective amount can range from about 9 μg/mL to about 20 μg/mL per 3 cm$^2$ of wound area. In some embodiments the effective amount can range from about 9 μg/mL per 3 cm$^2$ of wound area. In some embodiments the effective amount can range from about 18 μg/mL per 3 cm$^2$ of wound area. In some embodiments the effective amount can range from about 20 μg/mL per 3 cm$^2$ of wound area.

In yet other embodiments, the effective amount of the conditioned media, exosomes and/or an amount of purified MALAT1, VLDLR, or GAS5 lncRNA can range from about 1% w/w to about 99% or more w/w, w/v, or v/v of the total formulation. In some embodiments, the effective amount of the conditioned media, exosomes and/or an amount of purified MALAT1, VLDLR, or GAS5 lncRNA can be effective at increasing the rate of wound healing, cell proliferation increasing angiogenesis in the wound, and tissue remodeling.

In some embodiments, the effective amount of the pharmaceutical formulation can range from about 0.001 pg, 0.01 pg, 0.1 pg, 0.001 μg, 0.01 μg, 0.1 μg, 1 μg, 2 μg, 3 μg, 4 μg, 5 μg, 6 μg, 7 μg, 8 μg, 9 μg, 10 μg, 15 μg, 20 μg, 25 μg, 30 μg, 35 μg, 40 μg, 45 μg, 50 μg, 55 μg, 60 μg, 65 μg, 70 μg, 75 μg, 80 μg, 85 μg, 90 μg, 95 μg, 100 μg, 125 μg, 150 μg, 175 μg, 200 μg, 225 μg, 250 μg, 275 μg, 300 μg, 350 μg, 400 μg, 450 μg to about 500 μg or more or from about 0.01 pg/mL, 0.1, pg/mL, 1 μg/mL, 2 μg/mL, 3 μg/mL, 4 μg/mL, 5 μg/mL, 6 μg/mL, 7 μg/mL, 8 μg/mL, 9 μg/mL, 10 μg/mL, 15 μg/mL, 20 μg/mL, 25 μg/mL, 30 μg/mL, 35 μg/mL, 40 μg/mL, 45 μg/mL, 50 μg/mL, 55 μg/mL, 60 μg/mL, 65 μg/mL, 70 μg/mL, 75 μg/mL, 80 μg/mL, 85 μg/mL, 90 μg/mL, 95 μg/mL, 100 μg/mL, 125 μg/mL, 150 μg/mL, 175 μg/mL, 200 μg/mL, 225 μg/mL, 250 μg/mL, 275 μg/mL, 300 μg/mL, 350 μg/mL, 400 μg/mL, 450 μg/mL to about 500 μg/mL per cm$^2$ of wound area In some embodiments, the effective amount of the pharmaceutical formulation can be about 20 μg/mL per about 3 cm$^2$ of wound area. In some embodiments the effective amount of the pharmaceutical formulation can range from about 0.01 mL to 5 mL or more per cm$^2$ of wound area.

In some embodiments the exosomes, exosomal lncRNAs, or other compound described herein can be used in a medicament for the treatment and/or promotion of wound healing.

Methods of Using the Exosomes and Exosomal lncRNAs

An amount, including an effective amount, of the conditioned media, exosomes, and/or an amount of purified lncRNA and formulations thereof described herein can be administered to a subject in need thereof. In some embodiments the subject in need thereof can have a wound. The wound can be a recalcitrant, chronic, and/or ischemic wound.

Administration of the exosomes and/or purified MALAT1 lncRNA is not restricted to a single route, but can encompass administration by multiple routes. For instance, exemplary administrations by multiple routes include, among others, a combination of dermal, transdermal, topical, intradermal and intramuscular administration, or intradermal and subcutaneous administration. Multiple administrations can be sequential or concurrent. Other modes of application by multiple routes will be apparent to the skilled artisan.

The pharmaceutical formulations can be administered to a subject by any suitable method that allows the exosomes and/or an amount of purified MALAT1 lncRNA to exert its effect on the subject in vivo. For example, the formulations and other compositions described herein can be administered to the subject by known procedures including, but not limited to, by dermal, transdermal, topical, intravenous, and subcutaneous injection. Delivery can be by injection, infusion, catheter delivery, or some other means, such as by salve, lotion, gel, or spray.

In embodiments, the exosomes and/or purified MALAT1 lncRNA, or formulation thereof can be effective to treat a wound in a subject. In some embodiments, administration of the exosomes, lncRNAs, or formulations thereof can increase the rate of wound healing in the subject. In some embodiments, administration of the exosomes, lncRNAs, or formulations thereof can increase angiogenesis of the wound in the subject. It can increase cell proliferation, and tissue remodeling.

The exosomal and lncRNA compositions and formulations thereof provided herein can be administered to the subject one or more times. Where administration occurs more than once the time period between each does can each independently range from minutes, to hours (e.g. 1, 2, 4, 6, 8, 10, 12 or more hours), days (e.g. 1, 2, 3, 4, 5, 6, and/or 7 days), weeks (e.g. 1-52 weeks, or years (e.g. 1 to 2, 3, 4, 5, or more years) apart. Administration can occur during any life stage of the subject. Administration can be simultaneously or in series with other compounds or formulations (e.g. as a combination therapy). In some embodiments, administration can take place 1, 2, 4, 6, 8, 10, 12 or more hours), days (e.g. 1, 2, 3, 4, 5, 6, and/or 7 days), weeks (e.g. 1-52 weeks, or years (g. 1 to 2, 3, 4, 5, or more years) after wound formation in non-healing and recalcitrant wounds.

Combination Therapy

The pharmaceutical formulations or other compositions described herein can be administered to a subject either as a single agent, or in combination with one or more other agents. Additional agents include but are not limited to DNA, RNA, amino acids, peptides, polypeptides, antibodies, aptamers, ribozymes, guide sequences for ribozymes that inhibit translation or transcription of essential tumor proteins and genes, hormones, immunomodulators, antipyretics, anxiolytics, antipsychotics, analgesics, antispasmodics, anti-inflammatories, anti-histamines, anti-infectives, and chemotherapeutics.

EXAMPLES

Now having described the embodiments of the present disclosure, in general, the following Examples describe some additional embodiments of the present disclosure. While embodiments of the present disclosure are described in connection with the following examples and the corresponding text and figures, there is no intent to limit embodiments of the present disclosure to this description. On the contrary, the intent is to cover all alternatives, modifications, and equivalents included within the spirit and scope of embodiments of the present disclosure.

Example 1

Introduction

Chronically ill patients heal recalcitrant ulcerative wounds more slowly. Further, the Veterans Administration has a rapidly growing cohort of older veterans with diabetes and a new cohort of wounded veterans with injuries that include non-healing ulcers from spinal cord injury, multiple traumatic injuries and burns. Veteran populations are at risk for a staggering number of chronic wounds. Human adipose-derived stem cells (hADSC) play an important role in tissue regeneration and exosomes secreted by stem cells contribute to their paracrine signaling. A number of local and systemic factors impact wound healing including oxygenation, infection, age, and sex hormones, stress, diabetes, obesity, medications (e.g. chemotherapy), alcoholism, smoking, and nutrition. (8) The wound healing process includes four integrated and overlapping phases: hemostasis, inflammation, proliferation, and tissue remodeling (9). These must occur rapidly and appropriately in the proper sequence and continue for a specific duration for wound healing to occur successfully (10). Investigations and clinical studies have provided information about normal and impaired wound healing. In sum, oxygen levels are important for optimum wound healing. Hypoxia (low oxygen) stimulates the release of growth factors and angiogenesis, while oxygen is needed to sustain the process (11). Inflammation, a normal part of wound healing is important in the removal of microorganisms. Incomplete removal of bacteria and endotoxins can lead to infections at the injured skin surface, lengthening the inflammatory phase. Prolongation and escalation of the imnflammatory phase contributes to a failure to heal. It also leads to increased levels of matrix metalloproteinases that can degrade the extracellular matrix. Systemic factors also contribute to impaired wound healing (8).

The needs of a healing wound are complex and mediated by single and multiple factors that play roles in the individual features of healing that contribute to the overall outcome. Meshenchymal stem cells (MSC) derived from bone marrow can improve wound fibroblast migration in vitro (12). However, obtaining bone marrow is quite invasive and thus alternatives are desirable.

This Example describes compositions that can be effective as a therapy that can promote tissue regeneration and/or reverse the consequences of recalcitrant wounds. Additionally, this Example evaluates the role of lncRNA MALAT1 (metastasis-associated lung adenocarcinoma transcript 1), a lncRNA in exosomes that can be present in conditioned media from ADSC and ischemic wound healing. In some instances, conditioned medium (CM) from ADSC from normal (non-diseased) donors was used to evaluate the effect of stem cell secreted factors on fibroblast migration. Also, animal models were used to assess the effect of ADSC derived exosomes and lncRNA MALAT1 on healing in a model of traumatic brain injury (13). Exosomes, specific nanovesicles that can be secreted by stem cells, were isolated and the ability of secreted stem cell factors present in the exosomes to modify (e.g. increase) cell migration was evaluated. Exosomes can include many cargo proteins, lipids, RNAs, and other molecules. Exosomes can evade immune rejection by the host and can modify cellular responses (14).

A secreted nanovesicle from adipose derived stem cells (human ADSC) was used in the therapy. Human ADSC release trophic factors that can stimulate the endogenous repair mechanisms in wounds, have immunomodulatory effects, and can respond to the microenvironment (1, 2, 3). These factors have been shown to heal wounds. However, hADSC research is flawed by the lack of standardization and delivery methods (4).

This Example can demonstrate the effectiveness of stem cell regenerative secreted factors, such as exosomes and various lncRNAs, to heal wounds. The secreted factors can be contained in exosomes, which can act in a paracrine manner (FIG. 1). In particular, this Example focuses on the role of a new class of RNA, long-noncoding RNA MALAT1, and its potential role in cell migration, proliferation and angiogenesis via its interaction with microRNAs and proteins (5). Two models are used to demonstrate the effects of exosomes on wound healing. Without being bound to theory or example, it is believed that the collection and topical application of exosomes from hADSC can be a better treatment for difficult skin wounds because they can be stored at low temperatures and made available to wound care in non-clinical settings.

Materials and Methods

Unless otherwise described the following procedures were at least used.

Adult Human Dermal Fibroblast (HDF) culture: Adult-HDF were purchased from ScienCell (Catalog #2320). HDF, isolated from human skin, were negative for HIV-1, HCV, mycoplasma, bacteria, yeast, and fungi. Cells were expanded in Fibroblast Medium (FM, Cat #2301) according to manufacturer's protocol. Cells were subcultured in poly-L-lysine-coated culture vessels as recommended. Medium was changed every three days after plating until cells were 70% confluent and every other day until cell were 90% confluent.

Adipose derived stem cell (ADSC) culture and conditioned media (CM): Human ADSC were purchased from ZenBio, Inc. Cells were negative for HIV-1, HIV-2, HTLC-1, HTLV-2, Hep-B, Hep-C, and mycoplasma. Human ADSC were isolated from subcutaneous adipose tissue of normal, non-diabetic donors between the ages of 18-60 years undergoing elective surgery. They were cultured according to manufacturer. For CM collection, cells were grown to 90% confluence, media was replaced with chemically defined serum-free Mesenchymal Stem Cell Basal Media (MSCBM) (Lonza™), and CM was collected after about 48 hours.

Exosome Isolation: Exosomes were isolated using a two-step protocol. First, ExoQuick™ solution (SBI) was added to culture media at a volume of 1 to 5. Following centrifugation at 1,500 g for 30 min, the pellet was further processed. ExoCap™ (JSR Life Sciences) composite reagent containing magnetic beads for CD9, CD63 and CD81 was used to purify exosomes. Exosomes were eluted from beads using manufacturer's elution buffer and used in wound healing assays after washing twice with 500 HL washing buffer (15). To deplete MALAT from exosomes, cells were transfected with antisense oligonucleotides (ASO) as described (10). Scrambled ASO as described (16). Scrambled ASO were transfected as a control into ADSC, and CM was collected as described above. Exosomes were quantitated using a NanoSight LM10 (Malvern Instruments), and showed an average size of about 90-100 nm at a concentration of $1.1 \times 10^8$ per ml from $10^6$ cells CM (15, 16).

Scratch assays: HDF were plated in 24 well plates. The cells were grown to confluence and three days after confluence were mechanically disrupted with a sterile 200 μL pipette tip with the use of a grid of 3×3 mm squares scratched with a pipette tip as described (13). The pre-incubation with mitomycin C (10 μg/ml) for about 2 hrs blocks further proliferation so that only migration is followed.

ECIS assays: The ECIS or electric cell-substrate impedance sensing instrument (Applied Biophysics) recorded the impedance on electrically wounded hHDF to detect the migratory response. Briefly, 200 μl of cell suspension were seeded per well of 8W1E ECIS array ($5 \times 10^4$ cells per well) coated with about 1% gelatin. After cells were confluent in the incubator, the ECIS chambers were mounted to the ECIS system. Once the baseline leveled off, a 240 mA current with 60 KHz was applied to the cell-covered electrode for 30 seconds to kill the cells on the electrode (250 μm diameter), which resulted in dropping the impedance to around 2000. Arrays were then washed with medium under the microscope to remove any dead cells on the electrodes. Thereafter, the wound healing process was determined in real-time by measuring the recovery of electrical impedance, an indicator of the surrounding viable fibroblast cells migrating into the wounded area.

Rat Model of Ischemic Wound Healing: Young (6 month old) male Fischer 344 rats (National Institute on Aging, Bethesda, MD) were utilized to create an ischemic wound model (4). Full thickness excisional wounds were created in the center of a 10.5×3.5-cm flap (ischemic wounds) with a 6 mm punch biopsy and wound healing followed for about 2, 5, 7, 10, 14, and 21 days. Control (non-ischemic) full thickness wounds were created on either side of the ischemic flap for comparison. At the time of wounding and upon harvest, six rats were anesthetized, ischemic and non-ischemic wounds were digitally photographed, and wound sizes were determined 7. CM from ZenBio™ ADSC (20HI) or control (unconditioned) media (about 20 μL) was applied to each wound daily. On day 0 and on day 2, 5, 7, 10, and 21 wound sizes were determined.

Statistical Analysis: PRISM-6™ software was used for statistical analysis with appropriate tests for comparisons including one way ANOVA and unpaired t-test. Data are shown as mean±SEM. An n=3 is shown unless stated otherwise.

Results

Figure 3:
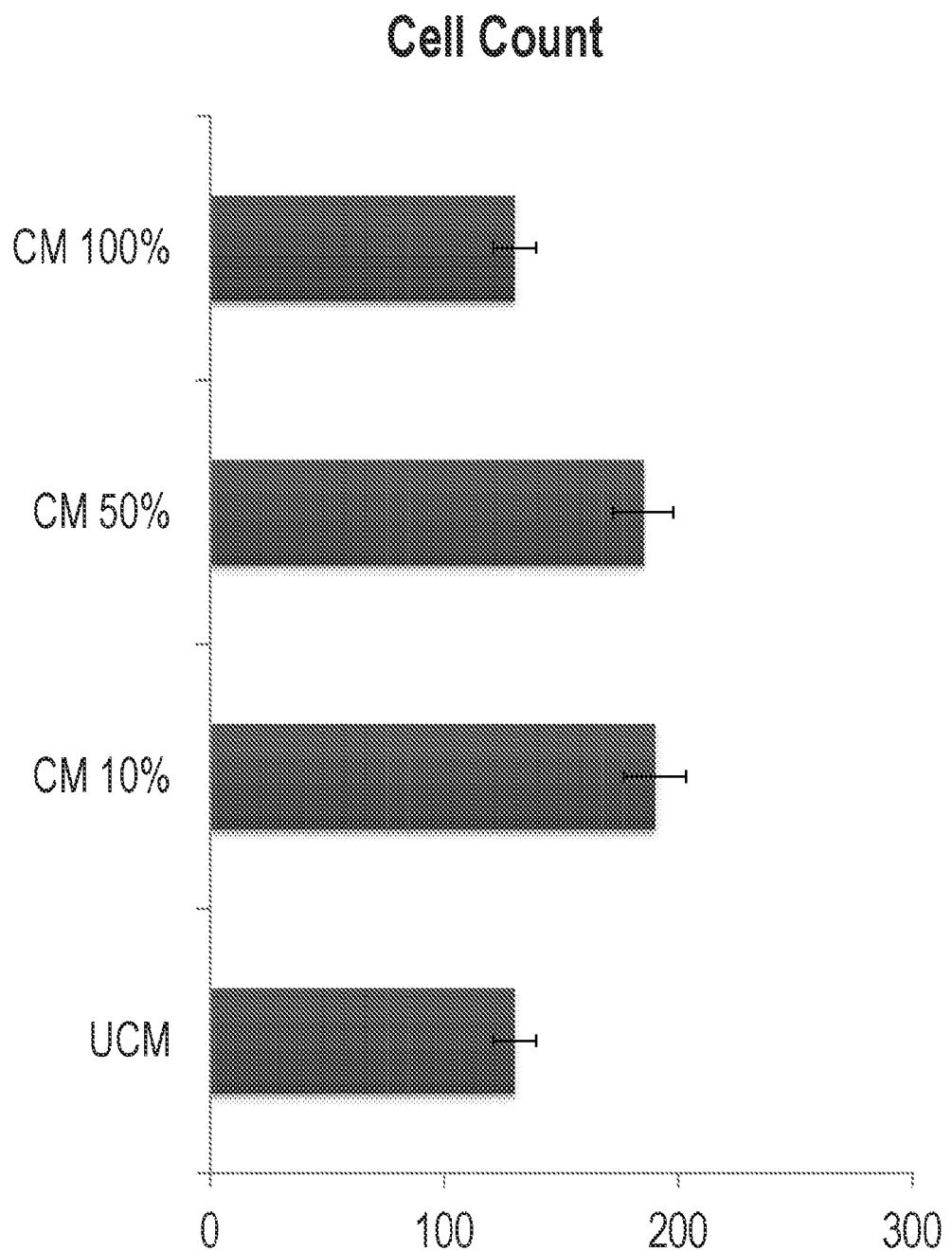
FIG. 3 shows a graph demonstrating the cell count of the cells under conditioned (FIGS. 4B, 4D, and 4F) or unconditioned medium (UCM) (FIG. 2B) at 18 h.
Figures 4A, 4B, 4C, 4D, 4E, 4F:
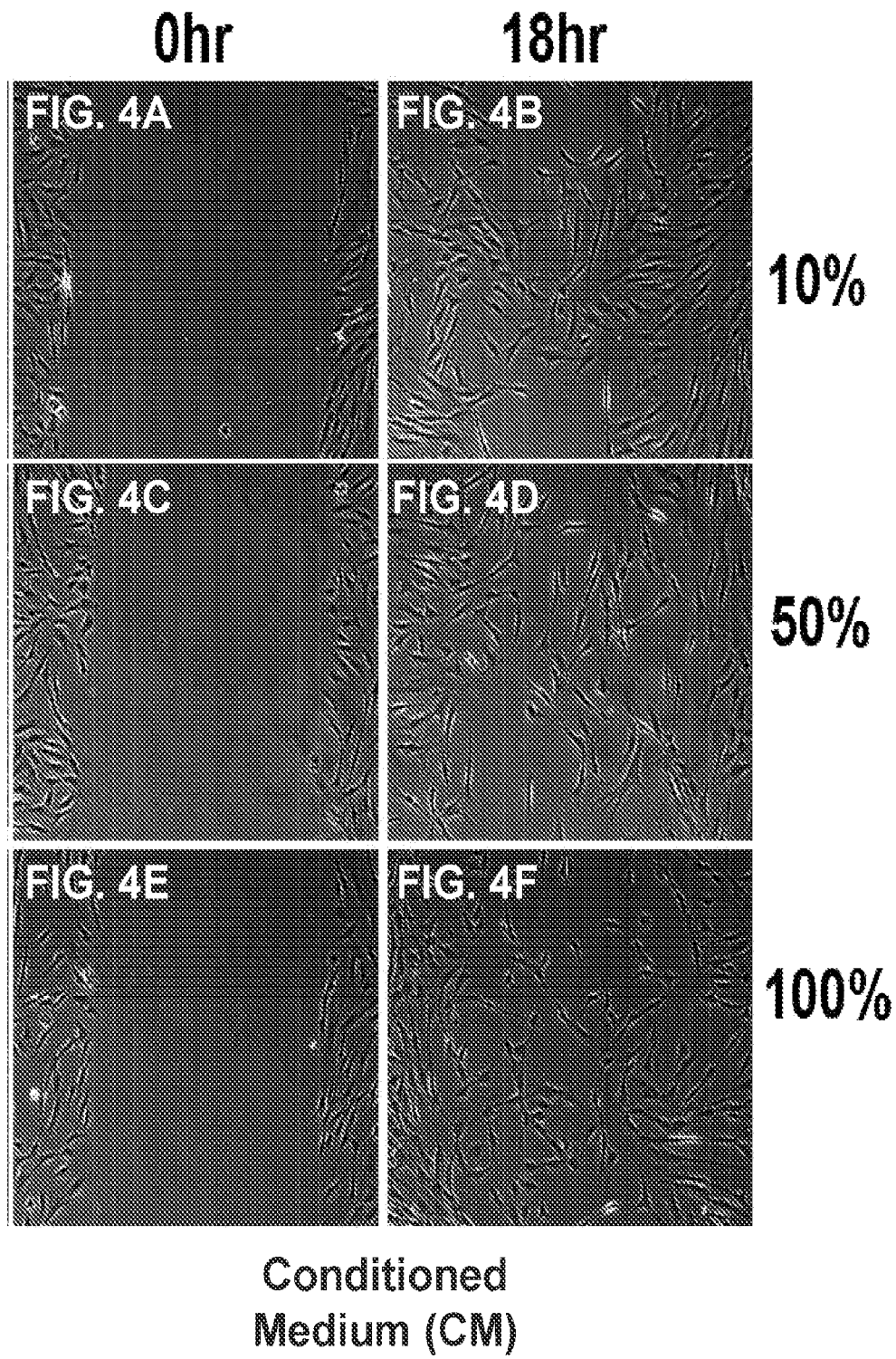
FIGS. 4A-4F show micrographic images demonstrating the results of a scratch assay to assess migration of young human dermal fibroblasts exposed to increasing concentrations of human adipose derived stem cell conditioned medium (hADSC-CM).

The results are demonstrated in FIGS. 2A-18. FIGS. 2A-2B and 4A-4F show micrographic images demonstrating the results of a scratch assay to assess migration of young human dermal fibroblasts exposed to increasing concentrations of human adipose derived stem cell conditioned medium (hADSC-CM) (FIGS. 4A-4F) or unconditioned medium (FIGS. 2A-2B). FIG. 3 shows a graph demonstrating the cell count of the cells under conditioned (FIGS. 4B, 4D, and 4F) or unconditioned medium (UCM) (FIG. 2B) at about 18 h. Briefly, CM was collected after about 48 h of exposure to hADSCs and stored at −80° C. Primary human dermal fibroblasts (HDFs) were grown to about 80% confluence and transferred to low serum DMEM for about 24 h. Proliferation was inhibited with mitomycin C and monolayers of HDF were scratched with a yellow pipette tip. Cultures were treated with ADSC-CM at increasing concentrations as shown in FIGS. 3-4F. Cell migration images were captured at 0 hours and at about 18 h.

Figure 5:
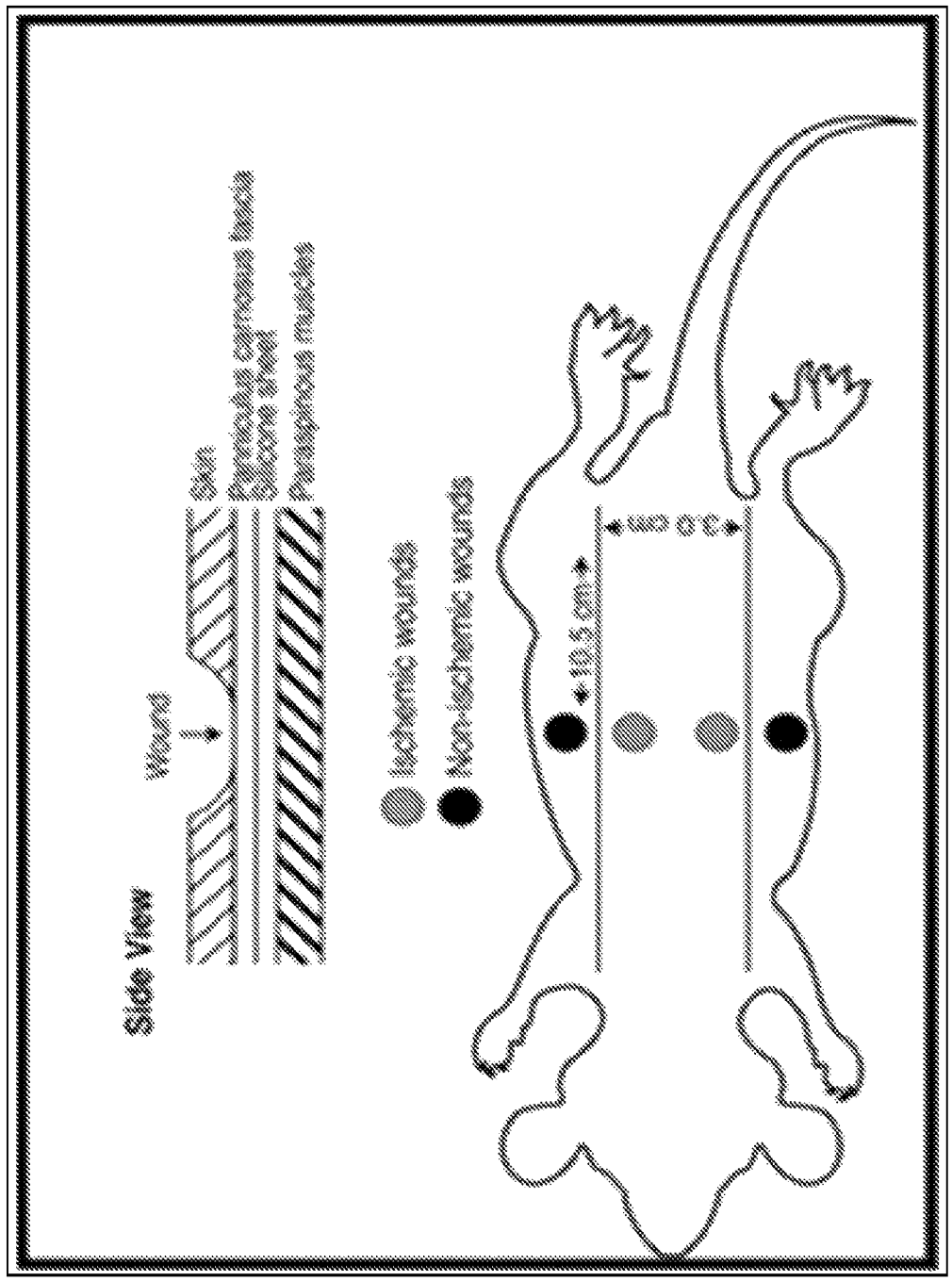
FIG. 5 shows an in vivo assay using a rat ischemic wound model modified for Fisher 344 rats.

FIG. 5 shows a cartoon demonstrating a rat ischemic wound model for Fisher 344 rats. The inset demonstrates placement of a silicone sheet. The 6 mm wounds are ischemic. Lateral wounds are not ischemic.

Figure 6:
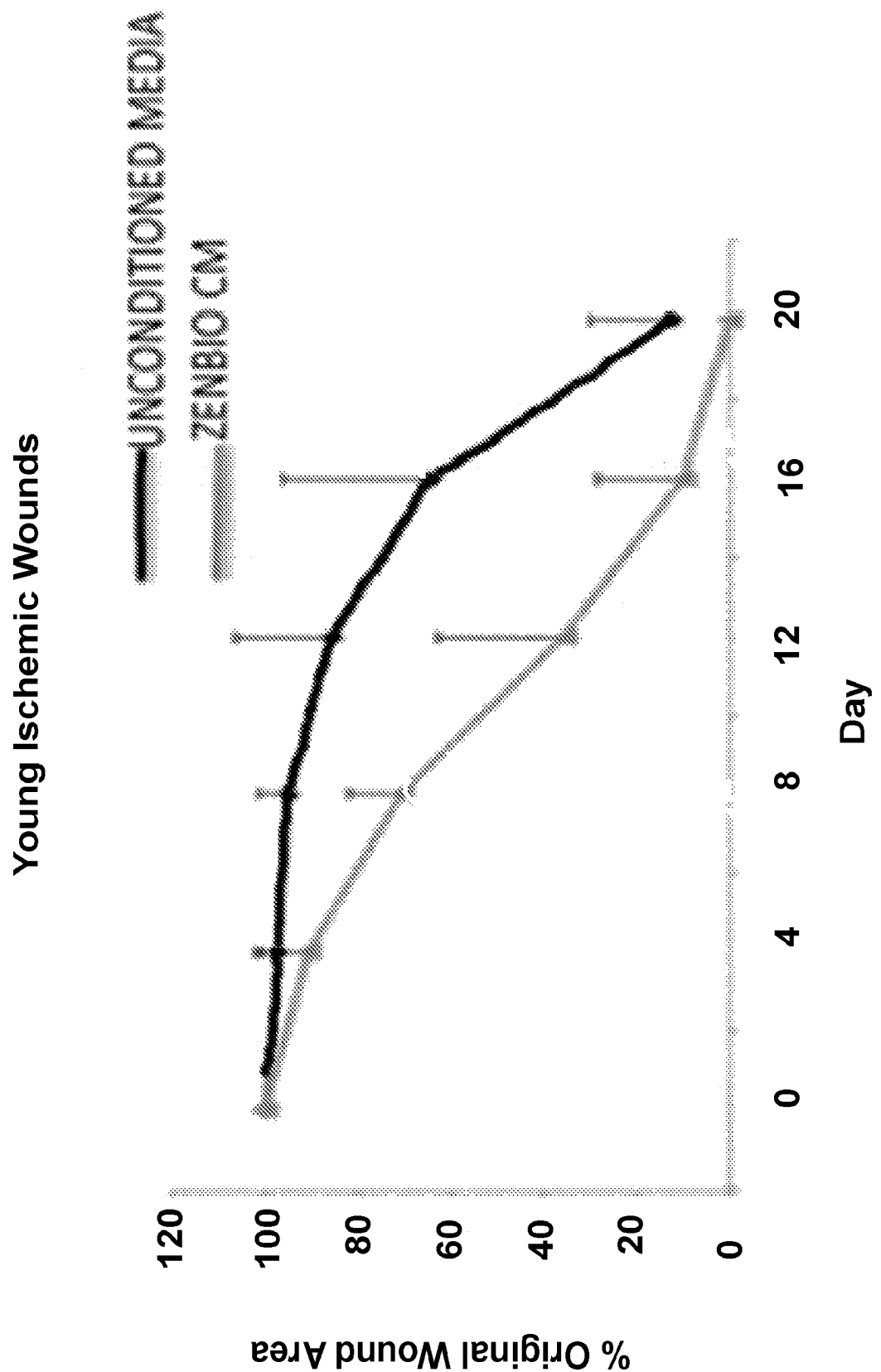
FIG. 6 shows a graph demonstrating the results from treatment of young ischemic wounds in a rat ischemic wound model as described and shown in reference to FIG. 5. Twenty-four Fisher rats underwent creation of a bipedicled ischemic flap with 6-mm excisional wounds, two ischemic and two nonischemic (control wound). Young adult (6 month old) rats were divided into groups of 6, comparing human ADSC-CM obtained from lean donors (Zenbio™). Twenty microliters of CM was applied topically daily to each wound beginning on the day of surgery. Digital photographs were taken every 4 days and wound area was measured using Image J. analysis revealed a statistically significant difference between control and lean conditioned media in ischemic wound sizes for days 8, 12, and 16 ($P<0.001$). 100% of lean CM treated ischemic wounds were healed at day 20, 50% of control media.
Figure 7:
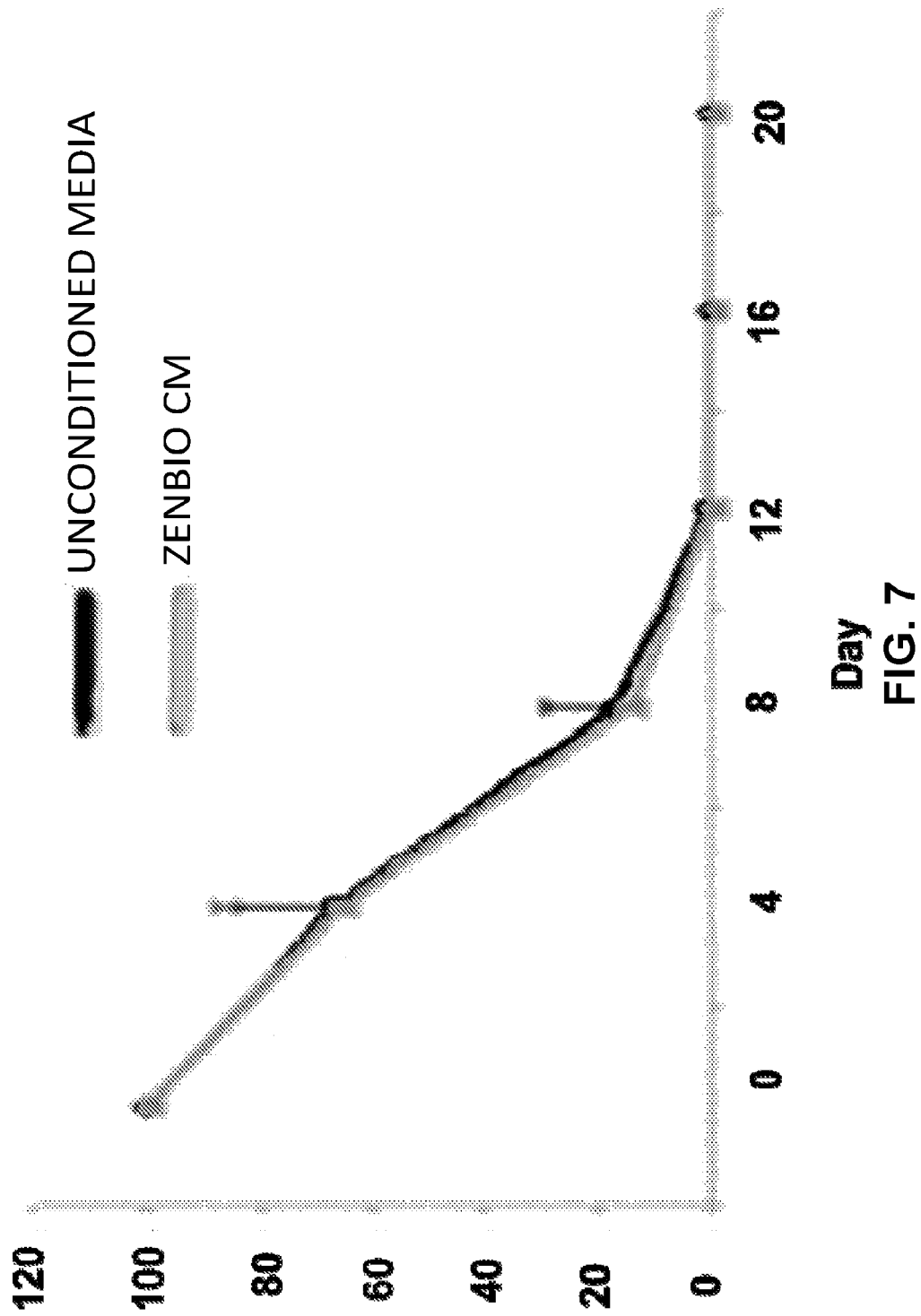
FIG. 7 shows a graph demonstrating the results from treatment of young nonischemic wounds in a rat ischemic wound model as described and shown in reference to FIG. 5.

FIGS. 6-7 show graphs demonstrating the results from treatment of wounds in a rat ischemic wound model as described and shown in reference to FIG. 5. Briefly, Twenty-four Fisher rats underwent creation of a bipedicled ischemic flap with 6-mm excisional wounds, two ischemic and two nonischemic (control wound). Rats were divided into groups of 6, comparing human ADSC-CM obtained from lean donors (ZenBio). Twenty microliters of CM was applied topically daily to each wound beginning on the day of surgery. Digital photographs were taken about every 4 days and wound area measured using Image J. Analysis revealed a statistically significant difference between control and lean conditioned media in ischemic wound sizes for days 8, 12 and 16 (p<0.001). 100% of lean CM treated ischemic wounds were healed at day 20, 50% of control media. (6)

Figure 8:
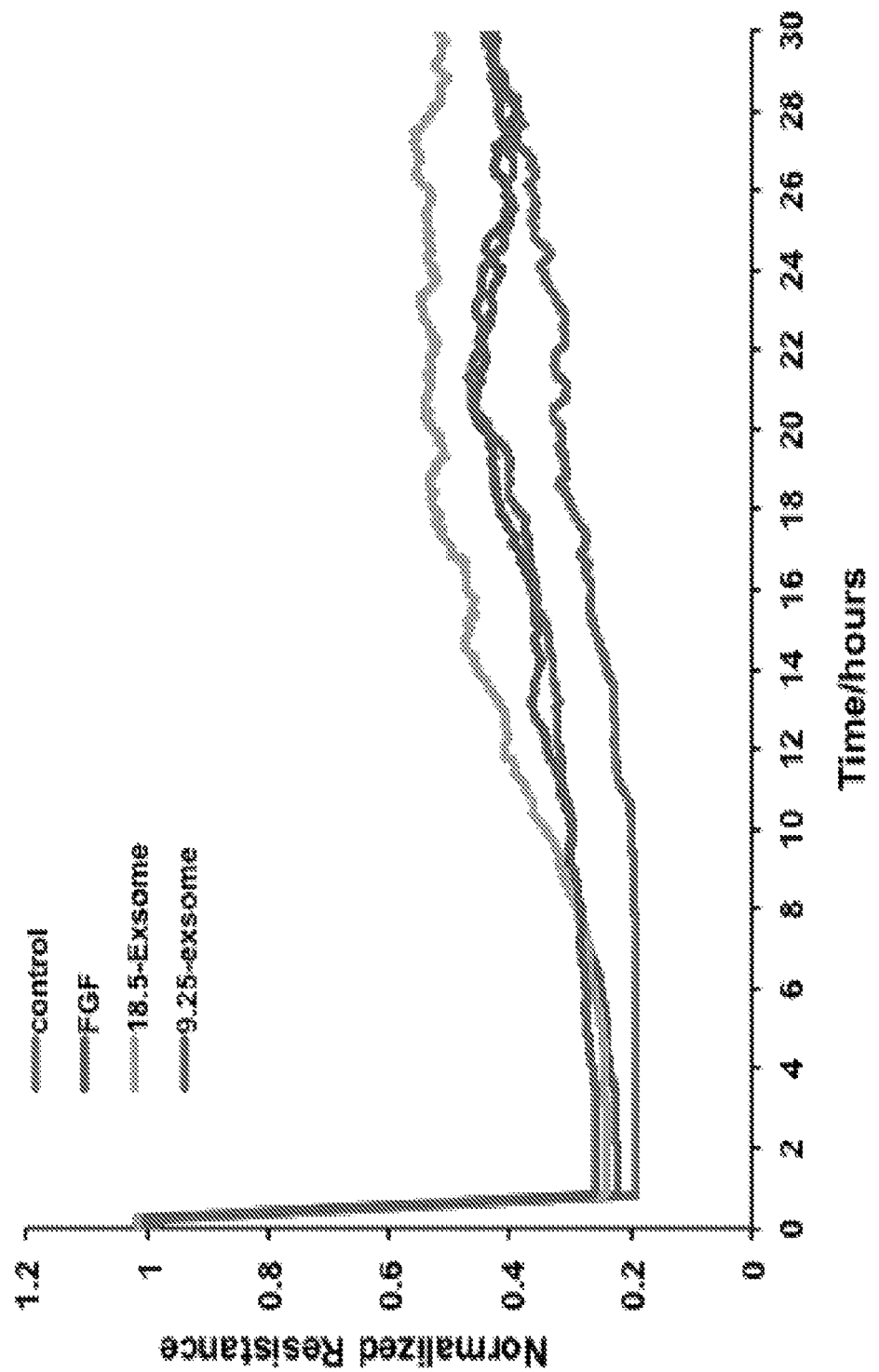
FIG. 8 shows a graph demonstrating the results of measuring the wound closure by electric cell-substrate impedance sensing (ECIS™).
Figure 9:
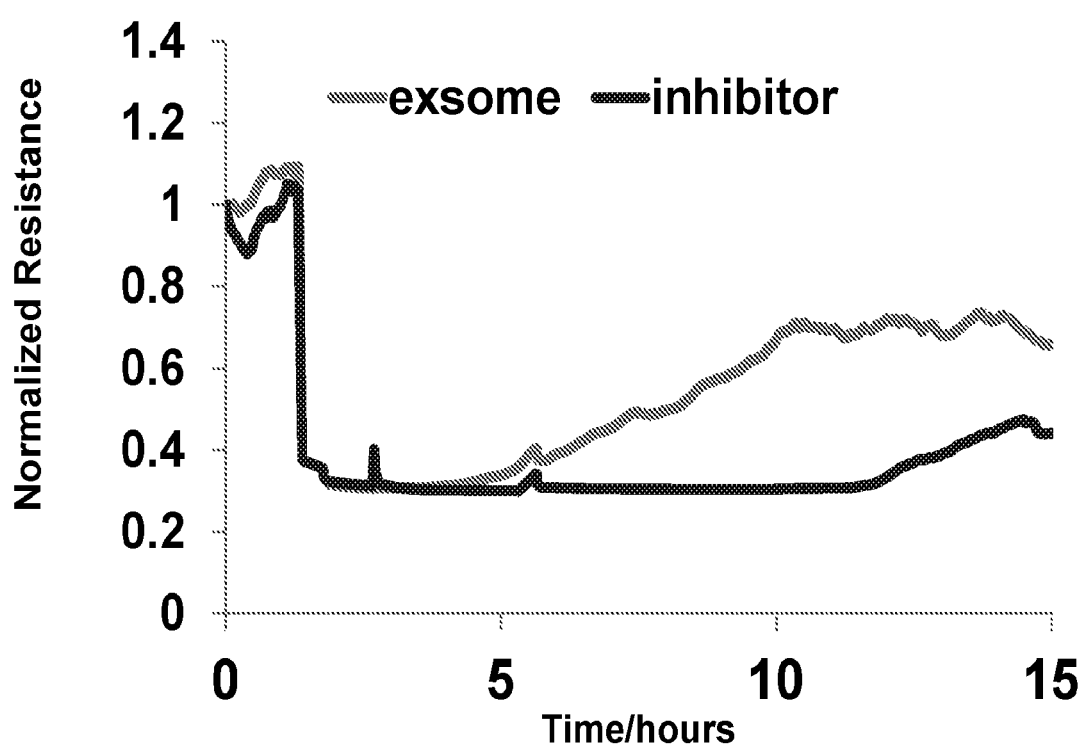
FIG. 9 shows a graph demonstrating the results of measuring the wound closure by electric cell-substrate impedance sensing (ECIS™) where the cells were treated with 20 µg of exosomes and were tested alone or in the presence of 50 µM dynasore. Briefly, human dermal fibroblast (HDF) cells on the microelectrodes of the ECIS wells were killed with a high electrical voltage. Subsequently, the migration of viable cells onto the wounded microelectrodes was measured in real-time by electrical resistance in the presence of 20 µg/L exosome, and then dynasore was added about 30 minutes later. The micrographs are normalized to the resistance before the wounding, N=3.

FIGS. 8-9 show graphs demonstrating the results of measuring the wound closure by electric cell-substrate impedance sensing (ECIS™). Normalized resistance over a time course for young HDFs exposed to two concentrations of purified exosomes (μg/ml) vs the hFGF (400 ng/ml) control, or control media. At zero time cells were "wounded" and additions were made. Resistance was followed for 30 hrs. The lower dose of the exosomes (about 9.25 μg/mL) increased resistance (cell migration) at the same rate as hFGF. The higher dose (about 18.5 μg/mL) increased resistance in a dose responsive manner, indicating that exosomes alone, were capable of enhancing wound healing in this in vitro model (n=2). In FIG. 9, 20 μg of exosomes were tested alone or in the presence of 50 μM Dynasore. Dynasore blocked the cell migratory effect of exosomes (n=2).

FIGS. 10A-10B show graphs demonstrating the RNA expression profile of several lncRNA and VLDLRs in conditioned medium (CM) and exosomes as detected by qRT-PCR. FIGS. 10A-10B show the relative quantification (RQ) of the RNA. Sc-ADSCn indicates normal subcutaneous stem cells. Ex indicates exosomes isolated from CM. Other lncRNA profiles of exosomes from ADSCs have also been examined.[7]

FIGS. 11A-13F demonstrate the results of antisense oligonucleotides (ASO) treatment on cells in CM as determined by a scratch assay. FIGS. 11A-11B and 13A-13D show micrographic images of the transfection control cells (FIGS. 11A-11B) and cells having knockdown of MALAT1 or NEAT 1 and the scramble control at 0 and 18 h (FIGS. 13A-13F). ADSC were treated with 500 nm of ASO (obtained via MTA from ISIS Pharmaceuticals). After 48 hrs, cells were switched to a serum free media and CM was collected for another 48 hrs. FIG. 12 shows a graph demonstrating the quantitative results from the dermal fibroblast migration tests in MALAT1 and NEAT 1 knockdown in cells cultured in conditioned medium at 18 h as imaged in FIGS. 11A-B and 13B, 13D, and 13F. Results are shown as of control.

FIG. 14 shows a graph demonstrating the effect of conditioned media from adipose derived stem cells (ADSC) on cell migration in human dermal fibroblasts. Briefly, young donor human dermal fibroblasts (HDF) were plated in 6 well dishes and when about 95% confluent, cells were scratched (3×) with a 200 μL pipette. Cells were treated with mitomycin C for about 2 h. Cell media from ZenBio ADSC was added (about 2 mL) for about 18 h. Unconditioned media (Lonza MSCMCD) was added as the control. After capturing images, migrating cells were counted in a field of the 3 scratch areas. PRISM™ analysis of the data indicated P<0.05.

FIG. 15 shows a graph demonstrating the number of cells counted in a field of the 3 scratch areas of FIGS. 13A-13F. After capturing images, migrating cells were counted in a field of the 3 scratch areas. PRISM™ analysis of the data indicated P<0.01.

FIG. 16 shows a graph demonstrating the effect of conditioned media from ADSC on HDF cell migration in an ECIS wounding assay. Briefly, HDF cells on the microelectrodes of the ECIS wells were killed with a high electrical voltage. Subsequently, the migration of viable cells onto the wounded microelectrodes was measured in real-time by electrical resistance in the presence of bFGF (about 400 nM), about 10 μg/mL exosomes, and about 20 μg/mL exosome respectively. The percentage of recovery was calculated by the difference in the resistance of each time point and the resistance of the first time point after wounding divided by the resistance before the wounding. The micrographs are representative of three ECIS wells at each time point.

FIG. 17 shows a graph demonstrating the effect of MALAT1 depletion on HDF cell migration as measured by an ECIS wound healing assay. Briefly, HDF cells on the micro-electrodes of the ECIS wells were killed with a high electrical voltage. Subsequently, the migration of viable cells into the wounded microelectrodes was measured in real-time by electrical resistance in the presence of bFGF (about 400 nM), 20 μg/mL exosome, about 20 μg/mL exosome-MALAT1 respectively. The micrographs are representative of three ECIS wells at each time point.

FIG. 18 shows a graph demonstrating the peak responses as cell migration rate from the HDF treatment groups described in relation to FIG. 17.

Conditioned media from ADSC can promote HDF cell migration. Fibroblasts interact with their environment to produce a migratory mode in wound healing. There are complex networks that occur thorough signals that drive the processes in wound healing. The in vitro scratch assay is a method for analysis of cell migration when cells are manipulated with transfection or micro-injection to assess the effects of exogenous factors on migration of individual cells (12). In a probe for the secreted factors from ADSC that modulate cell migration, CM from ZenBio™ normal subcutaneous derived ADSC were collected. CM was collected under stringent conditions using a serum-free, clinical grade media. This 48 h collection was termed ZenBio™ CM. ZenBio™ CM was compared to control or unconditioned Lonza MSCBM media. CM was observed to increase the migration of HDF in the scratch assay by about 43% (FIG. 14). This result indicated that ZenBio™ CM contained factor(s) that increased cell migration. The scratch assays demonstrated that human dermal fibroblasts when challenged with a "scratch" migrated into the scratch faster with the conditioned media than with unconditioned media (FIGS. 2A-4F and 14). Hence, stem cells secrete factors that increase cell migration.

Conditioned Media from ADSC can heal ischemic wounds in vivo. The in vitro results using CM from ADSC suggested that fibroblast migration, which can play a role in wound closure, was accelerated. ZenBio™ hADSC CM was applied to rat ischemic wounds to determine if the in vitro results would translate in vivo using a rat in vivo model. ZenBio™ ADSC CM was applied to ischemic and non-ischemic wounds for about 20 days and the percent of wound closure that occurred in each wound was measured (FIGS. 6-7). The results demonstrated that in young adult rats, ZenBio™ hADSC CM accelerated closure of ischemic wounds. By day 4, about a 66% reduction of wound area in non-ischemic (control) wounds was observed. By day 8, this had increased to about an 86% wound area reduction, and by day 12, the non-ischemic wounds were healed. For ischemic wounds, ZenBio™ ADSC CM treated wounds were 10% closed on day 4, on day 8, about 30% wound closure was measured, and by day 12, the wound area reduction was about 65% compared to only about 15% wound closure for the control (unconditioned) media treated wounds. Thus, ZenBio™ hADSC CM increased the ischemic wound closure by about 50% compared to non-ischemic wounds. This was actually more robust than expected based on the in vitro scratch assay results. The rat ischemic wound model reflected in vivo that conditioned media from hADSC, when applied at small quantities of 20 μl also resulted in healing ischemic wounds at a rate that mirrored the nonischemic or control wound (FIGS. 5-7).

Exosomes from CM simulated cell migration in ECIS assays. It was previously observed that ZenBio™ hADSC CM suppressed the recovery of rats injured with traumatic brain injury (17). In these experiments, CM was injected into the rats after injury and their ability to swim a water maze was improved. However, CM depleted of MALAT1 impaired this result. Here, the effect of depletion/reduction in CM was tested in young HDF. Depletion of MALAT1 in exosomes was accomplished using antisense oligonucleotides (ASO) to treat ZenBio™ hADSC with subsequent collection of CM. HDF trated with this CM resulted in reduction of cell migration of about 48% compared to CM from hADSC treated with the scrambled ASO (FIGS. 13A-13F and 15).

CM contains the ADSC secreted factors. The secretome of ADSC from CM contains a number of highly conserved proteins that have roles in angiogenesis, regeneration, and extracellular matrix remodeling (18). It was observed that exosomes isolated from CM contained in large concentrations of MALAT1 lncRNA (7, 20).

Exosomes can enhance cell migration. To evaluate the impact of CM exosomes on cell migration quantitatively, ECIS assays were employed (FIGS. 8-9 and 16). The concentration of exosomes applied was about equal to the number of exosomes found in the CM. For this assay, bFGF (about 400 nM) was used as a positive control as it is known to promote cell migration via the ERK1/2 abd Jnk pathways (21). The control (unconditioned media) and two doses of exosomes suspended in control media was then administered to injured to cells. FIG. 16 can demonstrate that the lower dose of the exosomes can increase recovery of transcellular electrical resistance (TER) similar to the effect of cells treated with bFGF. The higher concentration of exosomes was observed to enhance the recovery of TER faster and greater than the effect of bFGF. This indicated that exosomes promoted a strong effect on cell migration in the ECIS wound healing assay.

Dynasore can block the effect of exosomes. Extracellular exosomes have shown evidence that they can enter cells and deliver their cargo (19). The inhibitor, Dynasore, was added to determine if it blocked a clarthrin- and caveolin-dependent endocytosis of exosomes by the HDF. Dynasore (about 50 µM) addition to the exosome-containing media was observed to greatly attenuate cell migration (FIG. 9)

Exosomes isolated from MALAT1-depleted CM failed to enhance cell migration. The loss of function of MALAT1 in scratch assays was further demonstrated using exosomes derived from CM of hADSC treated with ASO. In this ECIS assay, resistance was measured in ohms. Treated cells were observed to have a significant increase of TER in comparison to cells treated with control media over a 16-hour course, which mimicked the effect of bFGF (about 400 nM) in the first 8 hours but displayed a greater rate of healing between hours 8 and 16. In cells treated with exosomes that were isolated from MALAT1 depleted hADSC, there was no observed significant effect on TER compared with control media (FIGS. 17-18). The result demonstrated importance of coexisting exosomes with MALAT1 in promoting cell migration and wound enclosure.

Discussion

The in vivo wound process is dynamic and consists of four continuous phases. In humans the relsease of pro-inflammatory cytokines such as bFGF is documented to occur prior to proliferation of fibroblasts within the wound bed to support angiogenesis (34). Treatement with CM from normal donor Zenbio™ ADSC was tested to determine if ischemic wounds heald at a greater rate than those treated with unconditioned or "control" media. It was observed that CM increased the rate of healing of HDF by a significant about 48%. This effect was mimicked in an animal model of ischemic wounds with results at days 12 and 16 that mirrored the effect of CM on cells. Levels of MALAT 1 in hADSC were also depleted using ASO. These hADSC produced CM that demonstrated about a 70% to about 90 reduction in MALAT1 content. This CM was tested in scratch assays and it was observed that CM with reduced MALAT1 content did not promote cell migration as well as the control media or CM from scrambled-ASO treated ADSC.

ECIS assays monitor real-time recovery of cell confluence after an electrically created wound by measureing the resistance of the wound area as resistance vs. time measured in these assays. ECIS assays demonstreated the ability of exosomes, isolated from CM, to increase migration of wounded cells. Migration was blocked using exosomes from CM of cells treated with MALAT1 ASO.

The diminished expression of MALAT1 by stem cells when treated with ASOs targeting this lncRNA resulted in a reduced secretion of MALAT1 into exosomes that was less than about 80% of the control. These depleted exosomes performed equally to "control" media in the ECIS assays. This followed the effect of MALAT1 ASO treated ADSC CM in the scratch assays. This data suggests that MALAT1 provided an important function in HDF migration in both assays evaluating CM and exosomes. Moreover, MALAT1 was taken up by the HDF as demonstrated by inhibition of migration when cells were treated with Dynasore, a blocker of clathrin- and caveolin-dependent endocytosis where dynamin-2 is the target (22, 23). The precise molecular mechanisms of MALAT1 action in determined. Its nuclear role is in alternative splicing of pre-mRNA (20). The effect of exosomes released from human iPSC from mesenchymal stem cells was shown to promote collagen synthesis and angiogenesis in vitro and in vivo (24). Exosomes promoted proliferation and migration of human umbilical vein endothelial cells. This occurred in a dose dependent manner where about 100 µg/mL of exosomes were used. In this Example, ten-fold lower concentrations of exosomes were observed to promote migration.

REFERENCES FOR EXAMPLE 1

1. (a) Wu, Y.; Wang, J.; Scott, P. G.; Tredget, E. E., Bone marrow-derived stem cells in wound healing: a review. *Wound Repair Regen* 2007, 15 Suppl 1, S18-26;
(b) Lim, J. S.; Yoo, G., Effects of adipose-derived stromal cells and of their extract on wound healing in a mouse model. *J Korean Med Sci* 2010, 25 (5), 746-51.
2. Kim, W. S.; Park, B. S.; Sung, J. H.; Yang, J. M.; Park, S. B.; Kwak, S. J.; Park, J. S. Wound healing effect of adipose-derived stem cells: a critical role of secretory factors on human dermal fibroblasts. *J Dermatol Sci* 2007, 48 (1), 15-24.
3. Kim, W. S.; Park, B. S.; Kim, H. K.; Park, J. S.; Kim, K. J.; Choi, J. S.; Chung, S. J.; Kim, D. D.; Sung, J. H., Evidence supporting antioxidant action of adipose-derived stem cells: protection of human dermal fibroblasts from oxidative stress. *J Dermatol Sci* 2008, 49 (2), 133-42.
4. Gould, L. J.; Leong, M.; Sonstein, J.; Wilson, S., Optimization and validation of an ischemic wound model. *Wound Repair Regen* 2005, 13 (6), 576-82.
5. (a) Wang, K. C.; Chang, H. Y., Molecular mechanisms of long noncoding RNAs. *Mol Cell* 2011, 43 (6), 904-14;
(b) Wapinski, O.; Chang, H. Y., Long noncoding RNAs and human disease. *Trends Cell Biol* 21 (6), 354-61.
6. Prather, J. L., Moor, A. N., Kesl, S. L., Jung, M. Y., Bickford, P. C., Cooper, D. R., Gould, L. J., Human adipose-derived stem cell conditioned media accelerates closure in an ischemic wound model. *Wound Rep Reg* 2013, 21, A39.
7. Patel et al., 2016. Stem Cell Invest. 3:2.

8. Guo, S. and Dipietro, L. A. (2010) J. Dent Res 89, 219-229.
9. Gosain, A. & DiPietro, L. A. (2004) Aging and wound healing. World J Surg 28, 321-326.
10. Mathieu, D. Role of hyperbaric oxygen therapy in the management of lower extremity wounds. (2006) Int J Low Extrem Wounds 5, 233-235.
11. Bishop, A. Role of oxygen in wound healing. J Wound Care 17, 399-402, (2008).
12. Liang, C. C., Park, A. Y. & Guan, J. L. In vitro scratch assay: a convenient and inexpensive method for analysis of cell migration in vitro. Nat Protoc 2, 329-333, (2007).
13. James, T. W., Wagner, R., White, L. A., Zwolak, R. M. & Brinckerhoff, C. E. Induction of collagenase and stromelysin gene expression by mechanical injury in a vascular smooth muscle-derived cell line. J Cell Physiol 157, 426-437, (1993).
14. Gupta, A. & Pulliam, L. Exosomes as mediators of neuroinflammation. J Neuroinflammation 11, 68, (2014).
15. Moor, A. N., Tummel, E., Prather, J. L., Jung, M., Lopez, J. J., Connors, S. & Gould, L. J. Consequences of age on ischemic wound healing in rats: altered antioxidant activity and delayed wound closure. Age (Dordr) 36, 733-748, (2014).
16. Ji, P., Diederichs, et al. MALAT-1, a novel noncoding RNA, and thymosin beta4 predict metastasis and survival in early-stage non-small cell lung cancer. Oncogene 22, 8031-8041, (2003).
17. Tajiri, N., et al. (2014) Intravenous transplants of human adipose-derived stem cell protect the brain from traumatic brain injury-induced neurodegeneration and motor and cognitive impairments: cell graft biodistribution and soluble factors in young and aged rats. J Neurosci 34, 313-326.
18. Kapur, S. K. & Katz, A. J. Review of the adipose derived stem cell secretome. Biochimie 95, 2222-2228, doi: 10.1016/j.biochi.2013.06.001 (2013).
19. Hu, L., Wang, J., Zhou, X., Xiong, Z., Zhao, J., Yu, R., Huang, F., Zhang, H. & Chen, L. Exosomes derived from human adipose mensenchymal stem cells accelerates cutaneous wound healing via optimizing the characteristics of fibroblasts. Sci Rep 6, 32993, (2016).
20. El Bassit, G., et al. MALAT1 in human adipose stem cells modulates survival and alternative splicing of PKCdeltaII in HT22 cells. Endocrinology, (2016).
21. Makino, T., et al. Basic fibroblast growth factor stimulates the proliferation of human dermal fibroblasts via the ERK1/2 and JNK pathways. Br. J Dermatol 162, 7171-723, (2010).
22. Hanson, S. E., Bentz, M. L. & Hematti, P. Mesenchymal stem cell therapy for nonhealing cutaneous wounds. Plast Reconstr Surg 125, 510-516, (2010).
23. Fitzner, D., et al. Selective transfer of exosomes from oligodendrocytes to microglia by macropinocytosis. J Cell Sci 124, 447-458, (2011).
24. Zhang, J., et al. Exosomes released from human induced pluripotent stem cells-derived MSCs facilitate cutaneous wound healing by promoting collagen synthesis and angiogenesis. J Transl Med 13, 49, (2015).

We claim:

1. A pharmaceutical formulation for increasing the rate of recalcitrant wound healing in a subject in need thereof, the formulation comprising an effective amount of exosomes comprising lncRNA, wherein the exosomes are derived from adipose stem cells obtained from a lean subject,
wherein the lncRNA is MALAT1 lncRNA and VLDLR lncRNA or MALAT1 lncRNA and GAS5 lncRNA
wherein the concentration of MALAT1 lncRNA is greater than the concentration of VLDLR lncRNA or GAS5 lncRNA and the effective amount can range from 0.001 pg to 500 µg or more, and
wherein the MALAT1 lncRNA has a sequence that is about 95-100% identical to SEQ ID NO.: 1 or is a fragment of at least 20 contiguous nucleotides that are 95-100% identical to SEQ ID NO: 1,
wherein the VLDLR lncRNA has a sequence that is 90-100% identical to SEQ ID NO.: 2 or is a fragment of at least 20 contiguous nucleotides that are 95-100% identical to SEQ ID NO: 2; and
wherein the GAS5 lncRNA has a sequence that is 90-100% identical to SEQ ID NO.: 3 or is a fragment of at least 20 contiguous nucleotides that are 95-100% identical to SEQ ID NO: 3; and
a pharmaceutically acceptable carrier.

2. The pharmaceutical formulation of claim 1, wherein the effective amount ranges from about 0.001 pg/mL to about 500 µg/mL.

3. The pharmaceutical formulation of claim 1, wherein the recalcitrant wound is chronic.

4. The pharmaceutical formulation of claim 1, wherein the recalcitrant wound is due to non-healing ulcers from spinal cord injury, multiple traumatic injuries, or burns.

5. The pharmaceutical formulation of claim 1, wherein the subject in need thereof is a subject with a chronic illness.

6. A method of treating a recalcitrant wound in a human subject in need thereof, the method comprising:
administering to the recalcitrant wound a pharmaceutical formulation comprising exosomes comprising lncRNA, wherein the exosomes are derived from adipose stem cells obtained from a lean subject,
wherein the lncRNA comprises MALAT1 lncRNA and VLDLR lncRNA or MALAT1 lncRNA and GAS5 lncRNA, wherein the concentration of MALAT1 lncRNA is greater than the concentration of VLDLR lncRNA or GAS5 lncRNA, and a pharmaceutically acceptable carrier,
wherein the pharmaceutical formulation is administered either topically or through direct injection at the wound site to the human subject in need thereof,
wherein the amount of MALAT1, VLDLR, or GAS5 lncRNA is an effective amount sufficient to increase the rate of recalcitrant wound healing compared to exosomes without the lncRNA.

7. The method of claim 6, wherein the amount of the pharmaceutical formulation is administered topically.

8. The method of claim 6, wherein the amount of the pharmaceutical formulation is administered directly to the wound.

9. The method of claim 6, wherein the administration can occur one or more times.

10. The method of claim 6, wherein the MALAT1 lncRNA has a sequence that is about 95-100% identical to SEQ ID NO.: 1 or is a fragment of at least 20 contiguous nucleotides that are 95-100% identical to SEQ ID NO: 1,
wherein the VLDLR lncRNA has a sequence that is 90-100% identical to SEQ ID NO.: 2 or is a fragment of at least 20 contiguous nucleotides that are 95-100% identical to SEQ ID NO: 2; and
wherein the GAS5 lncRNA has a sequence that is 90-100% identical to SEQ ID NO.: 3 or is a fragment of at least 20 contiguous nucleotides that are 95-100% identical to SEQ ID NO: 3.

11. The method of claim 6, wherein the recalcitrant wound is chronic.

12. The method of claim 6, wherein the recalcitrant wound is due to non-healing ulcers from spinal cord injury, multiple traumatic injuries, or burns.

13. The method of claim 6, wherein the subject in need thereof is a subject with a chronic illness.

* * * * *

SEQUENCE LISTING

```
<160> NUMBER OF SEQ ID NOS: 3

<210> SEQ ID NO 1
<211> LENGTH: 8758
<212> TYPE: DNA
<213> ORGANISM: Artificial Sequence
<220> FEATURE:
<223> OTHER INFORMATION: Malat1, NCBI Reference Sequence Accession No.:
      NR_002819.3; Homo sapiens metastasis associated lung
      adenocarcinoma transcript 1 (non-protein coding) (MALAT1), long
      non-coding RNA

<400> SEQUENCE: 1
gtaaaggact ggggcccgc  aactggcctc tcctgccctc ttaagcgcag cgccatttta      60
gcaacgcaga agcccggcgc cgggaagcct cagctcgcct gaaggcaggt ccctctgac     120 gcctccggga gcccaggttt cccagagtcc ttgggacgca gcgacgagtt gtgctgctat    180
cttagctgtc cttataggct ggccattcca ggtggtggta tttagataaa accactcaaa    240
ctctgcagtt tggtcttggg gtttggagga aagcttttat ttttcttcct gctccggttc    300
agaaggtctg aagctcatac ctaaccaggc ataacacaga atctgcaaaa caaaaacccc    360
taaaaaagca gacccagagc agtgtaaaca cttctgggtg tgtccctgac tggctgccca    420
aggtctctgt gtcttcggag acaaagccat tcgcttagtt ggtctacttt aaaaggccac    480
ttgaactcgc tttccatggc gatttgcctt gtgagcactt tcaggagagc ctggaagctg    540
aaaaacggta gaaaatttc cgtgcgggcc gtggggggct ggcggcaact ggggggccgc     600
agatcagagt gggccactgg cagccaacgg cccccggggc tcaggcgggg agcagctctg    660
tggtgtggga ttgaggcgtt ttccaagagt gggttttcac gtttctaaga tttcccaagc    720
agacagcccg tgctgctccg atttctcgaa caaaaaagca aaacgtgtgg ctgtcttggg    780
```

```
agcaagtcgc aggactgcaa gcagttgggg gagaaagtcc gccattttgc cacttctcaa    840
ccgtccctgc aaggctgggg ctcagttgcg taatggaaag taaagccctg aactatcaca    900
ctttaatctt ccttcaaaag gtggtaaact atacctactg tccctcaaga gaacacaaga    960
agtgctttaa gaggtatttt aaaagttccg ggggttttgt gaggtgtttg atgacccgtt   1020
taaaatatga tttccatgtt tcttttgtct aaagtttgca gctcaaatct ttccacacgc   1080
tagtaattta agtatttctg catgtgtagt ttgcattcaa gttccataag ctgttaagaa   1140
aaatctagaa aagtaaaact agaacctatt tttaaccgaa gaactacttt ttgcctccct   1200
cacaaaggcg gcggaaggtg atcgaattcc ggtgatgcga gttgttctcc gtctataaat   1260
acgcctcgcc cgagctgtgc ggtaggcatt gaggcagcca gcgcaggggc ttctgctgag   1320
ggggcaggcg gagcttgagg aaaccgcaga taagttttt tctctttgaa agatagagat   1380
taatacaact acttaaaaaa tatagtcaat aggttactaa gatattgctt agcgttaagt   1440
ttttaacgta atttaatag cttaagattt taagagaaaa tatgaagact tagaagagta    1500
gcatgaggaa ggaaaagata aaaggtttct aaaacatgac ggaggttgag atgaagcttc   1560
ttcatggagt aaaaaatgta tttaaaagaa aattgagaga aaggactaca gagccccgaa   1620
ttaataccaa tagaagggca atgcttttag attaaaatga aggtgactta aacagcttaa   1680
agtttagttt aaaagttgta ggtgattaaa ataatttgaa ggcgatcttt taaaaagaga   1740
ttaaaccgaa ggtgattaaa agaccttgaa atccatgacg cagggagaat tgcgtcattt   1800
aaagcctagt taacgcattt actaaacgca gacgaaaatg gaaagattaa ttgggagtgg   1860
taggatgaaa caatttggag aagatagaag tttgaagtgg aaaactggaa gacagaagta   1920
cgggaaggcg aagaaaagaa tagagaagat agggaaatta aagataaaa acatactttt   1980
agaagaaaaa agataaattt aaacctgaaa agtaggaagc agaagaaaaa agacaagcta   2040
ggaaacaaaa agctaagggc aaaatgtaca aacttagaag aaaattggaa gatagaaaca   2100
agatagaaaa tgaaaatatt gtcaagagtt tcagatagaa aatgaaaaac aagctaagac   2160
aagtattgga gaagtataga agatagaaaa atataaagcc aaaaattgga taaaatagca   2220
ctgaaaaaat gaggaaatta ttggtaacca atttatttta aaagcccatc aatttaatt   2280
ctggtggtgc agaagttaga aggtaaagct tgagaagatg agggtgttta cgtagaccag   2340
aaccaattta gaagaatact tgaagctaga aggggaagtt ggttaaaaat cacatcaaaa   2400
agctactaaa aggactggtg taatttaaaa aaaactaagg cagaaggctt ttggaagagt   2460
tagaagaatt tggaaggcct taaatatagt agcttagttt gaaaaatgtg aaggactttc   2520
gtaacggaag taattcaaga tcaagagtaa ttaccaactt aatgttttg cattggactt    2580
tgagttaaga ttatttttta aatcctgagg actagcatta attgacagct gacccaggtg   2640
ctacacagaa gtggattcag tgaatctagg aagacagcag cagacaggat tccaggaacc   2700
agtgtttgat gaagctagga ctgaggagca agcgagcaag cagcagttcg tggtgaagat   2760
aggaaaagag tccaggagcc agtgcgattt ggtgaaggaa gctaggaaga aggaaggagc   2820
gctaacgatt tggtggtgaa gctaggaaaa aggattccag gaaggagcga gtgcaatttg   2880
gtgatgaagg tagcaggcgg cttggcttgg caaccacacg gaggaggcga gcaggcgttg   2940
tgcgtagagg atcctagacc agcatgccag tgtgccaagg ccacagggaa agcgagtggt   3000
tggtaaaaat ccgtgaggtc ggcaaatgt tgttttctg gaacttactt atggtaacct    3060
tttatttatt ttctaatata atgggggagt ttcgtactga ggtgtaaagg gatttatatg   3120
gggacgtagg ccgatttccg ggtgttgtag gtttctcttt ttcaggctta tactcatgaa   3180
```

```
tcttgtctga agcttttgag ggcagactgc caagtcctgg agaaatagta gatggcaagt    3240
ttgtgggttt tttttttta cacgaatttg aggaaaacca aatgaatttg atagccaaat    3300
tgagacaatt tcagcaaatc tgtaagcagt ttgtatgttt agttggggta atgaagtatt    3360
tcagttttgt gaatagatga cctgttttta cttcctcacc ctgaattcgt tttgtaaatg    3420
tagagtttgg atgtgtaact gaggcggggg ggagttttca gtattttttt ttgtgggggt    3480
gggggcaaaa tatgttttca gttctttttc ccttaggtct gtctagaatc ctaaaggcaa    3540
atgactcaag gtgtaacaga aaacaagaaa atccaatatc aggataatca gaccaccaca    3600
ggtttacagt ttatagaaac tagagcagtt ctcacgttga ggtctgtgga agagatgtcc    3660
attggagaaa tggctggtag ttactctttt ttccccccac ccccttaatc agactttaaa    3720
agtgcttaac cccttaaact tgttattttt tacttgaagc attttgggat ggtcttaaca    3780
gggaagagag agggtggggg agaaaatgtt ttttctaag attttccaca gatgctatag    3840
tactattgac aaactgggtt agagaaggag tgtaccgctg tgctgttggc acgaacacct    3900
tcagggactg gagctgcttt tatccttgga agagtattcc cagttgaagc tgaaaagtac    3960
agcacagtgc agctttggtt catattcagt catctcagga gaacttcaga agagcttgag    4020
taggccaaat gttgaagtta agttttccaa taatgtgact tcttaaaagt tttattaaag    4080
gggaggggca atattggca attagttggc agtggcctgt tacggttggg attggtgggg    4140
tgggtttagg taattgttta gtttatgatt gcagataaac tcatgccaga gaacttaaag    4200
tcttagaatg gaaaaagtaa agaaatatca acttccaagt tggcaagtaa ctcccaatga    4260
tttagttttt ttcccccccag tttgaattgg gaagctgggg gaagttaaat atgagccact    4320
gggtgtacca gtgcattaat ttgggcaagg aaagtgtcat aatttgatac tgtatctgtt    4380
ttccttcaaa gtatagagct ttttggggaag gaaagtattg aactgggggt tggtctggcc    4440
tactgggctg acattaacta caattatggg aaatgcaaaa gttgtttgga tatggtagtg    4500
tgtggttctc ttttggaatt ttttttcaggt gatttaataa taatttaaaa ctactataga    4560
aactgcagag caaaggaagt ggcttaatga tcctgaaggg atttcttctg atggtagctt    4620
ttgtattatc aagtaagatt ctattttcag ttgtgtgtaa gcaagttttt ttttagtgta    4680
ggagaaatac ttttccattg tttaactgca aaacaagatg ttaaggtatg cttcaaaaat    4740
tttgtaaatt gtttatttta aacttatctg tttgtaaatt gtaactgatt aagaattgtg    4800
atagttcagc ttgaatgtct cttagagggt gggcttttgt tgatgaggga ggggaaactt    4860
tttttttttc tatagacttt tttcagataa catcttctga gtcataacca gcctggcagt    4920
atgatggcct agatgcagag aaaacagctc cttggtgaat tgataagtaa aggcagaaaa    4980
gattatatgt catacctcca ttggggaata agcataaccc tgagattctt actactgatg    5040
agaacattat ctgcatatgc caaaaatttt taagcaaatg aaagctacca atttaaagtt    5100
acggaatcta ccatttaaaa gttaattgct tgtcaagcta taaccacaaa aataatgaat    5160
tgatgagaaa tacaatgaag aggcaatgtc catctcaaaa tactgctttt acaaaagcag    5220
aataaaagcg aaagaaatg aaaatgttac actacattaa tcctggaata aaagaagccg    5280
aaataaatga gagatgagtt gggatcaagt ggattgagga ggctgtgctg tgtgccaatg    5340
tttcgtttgc ctcagacagg tatctcttcg ttatcagaag agttgcttca tttcatctgg    5400
gagcagaaaa cagcaggcag ctgttaacag ataagtttaa cttgcatctg cagtattgca    5460
tgttagggat aagtgcttat ttttaagagc tgtggagttc ttaaatatca accatggcac    5520
```

```
tttctcctga cccctcccct aggggatttc aggattgaga aattttttca tcgagccttt    5580
ttaaaattgt aggacttgtt cctgtgggct tcagtgatgg gatagtacac ttcactcaga    5640
ggcatttgca tctttaaata atttcttaaa agcctctaaa gtgatcagtg ccttgatgcc    5700
aactaaggaa atttgtttag cattgaatct ctgaaggctc tatgaaagga atagcatgat    5760
gtgctgttag aatcagatgt tactgctaaa atttacatgt tgtgatgtaa attgtgtaga    5820
aaaccattaa atcattcaaa ataataaact attttatta gagaatgtat acttttagaa     5880
agctgtctcc ttatttaaat aaaatagtgt ttgtctgtag ttcagtgttg ggcaatctt     5940
ggggggatt cttctctaat ctttcagaaa ctttgtctgc gaacactctt taatggacca     6000
gatcaggatt tgagcggaag aacgaatgta actttaaggc aggaaagaca aattttattc    6060
ttcataaagt gatgagcata taataattcc aggcacatgg caatagaggc cctctaaata    6120
aggaataaat aacctcttag acaggtggga gattatgatc agagtaaaag gtaattacac    6180
attttatttc cagaaagtca ggggtctata aattgacagt gattagagta atactttttc    6240
acatttccaa agtttgcatg ttaacttaa atgcttacaa tcttagagtg gtaggcaatg      6300
ttttacacta ttgaccttat atagggaagg aggggggtgc ctgtggggtt ttaaagaatt    6360
ttcctttgca gaggcatttc atccttcatg aagccattca ggattttgaa ttgcatatga    6420
gtgcttggct cttccttctg ttctagtgag tgtatgagac cttgcagtga gtttatcagc    6480
atactcaaaa ttttttcct ggaatttgga gggatgggag gaggggtgg ggcttacttg       6540
ttgtagcttt ttttttttt acagacttca cagagaatgc agttgtcttg acttcaggtc     6600
tgtctgttct gttggcaagt aaatgcagta ctgttctgat cccgctgcta ttagaatgca    6660
ttgtgaaacg actggagtat gattaaaagt tgtgttcccc aatgcttgga gtagtgattg    6720
ttgaaggaaa aaatccagct gagtgataaa ggctgagtgt tgaggaaatt tctgcagttt    6780
taagcagtcg tatttgtgat tgaagctgag tacattttgc tggtgtattt ttaggtaaaa    6840
tgcttttgt tcatttctgg tggtgggagg ggactgaagc ctttagtctt ttccagatgc      6900
aaccttaaaa tcagtgacaa gaaacattcc aaacaagcaa cagtcttcaa gaaattaaac    6960
tggcaagtgg aaatgtttaa acagttcagt gatcttagt gcattgttta tgtgtgggtt      7020
tctctctccc ctcccttggt cttaattctt acatgcagga acactcagca gacacacgta    7080
tgcgaagggc cagagaagcc agacccagta agaaaaaata gcctatttac tttaaataaa    7140
ccaaacattc cattttaaat gtggggattg gaaccacta gttcttcag atggtattct       7200
tcagactata gaaggagctt ccagttgaat tcaccagtgg acaaaatgag gaaaacaggt    7260
gaacaagctt tttctgtatt tacatacaaa gtcagatcag ttatgggaca atagtattga    7320
atagatttca gctttatgct ggagtaactg gcatgtgagc aaactgtgtt ggcgtggggg    7380
tggaggggtg aggtgggcgc taagcctttt tttaagattt tcaggtacc cctcactaaa     7440
ggcaccgaag gcttaaagta ggacaaccat ggagccttcc tgtggcagga gagacaacaa    7500
agcgctatta tcctaaggtc aagagaagtg tcagcctcac ctgatttta ttagtaatga     7560
ggacttgcct caactccctc tttctggagt gaagcatccg aaggaatgct tgaagtaccc    7620
ctgggcttct cttaacattt aagcaagctg ttttatagc agctcttaat aataaagccc     7680
aaatctcaag cggtgcttga aggggaggga aaggggaaa gcggcaacc acttttccct      7740
agcttttcca gaagcctgtt aaaagcaagg tctccccaca agcaacttct ctgccacatc    7800
gccaccccgt gccttttgat ctagcacaga cccttcaccc ctcacctcga tgcagccagt    7860
agcttggatc cttgtgggca tgatccataa tcggtttcaa ggtaacgatg gtgtcgaggt    7920
```

```
ctttggtggg ttgaactatg ttagaaaagg ccattaattt gcctgcaaat tgttaacaga    7980
agggtattaa aaccacagct aagtagctct attataatac ttatccagtg actaaaacca    8040
acttaaacca gtaagtggag aaataacatg ttcaagaact gtaatgctgg gtgggaacat    8100
gtaacttgta gactggagaa gataggcatt tgagtggctg agagggcttt tgggtgggaa    8160
tgcaaaaatt ctctgctaag acttttttcag gtgaacataa cagacttggc caagctagca   8220
tcttagcgga agctgatctc caatgctctt cagtagggtc atgaaggttt tcttttcct     8280 gagaaaacaa cacgtattgt tttctcaggt tttgcttttt ggcctttttc tagcttaaaa    8340
aaaaaaaaag caaagatgc tggtggttgg cactcctggt ttccaggacg gggttcaaat     8400
ccctgcggcg tctttgcttt gactactaat ctgtcttcag gactctttct gtatttctcc    8460
ttttctctgc aggtgctagt tcttggagtt ttggggaggt gggaggtaac agcacaatat    8520
ctttgaacta tatacatcct tgatgtataa tttgtcagga gcttgacttg attgtatatt    8580
catatttaca cgagaaccta atataactgc cttgtctttt tcaggtaata gcctgcagct    8640
ggtgttttga gaagccctac tgctgaaaac ttaacaattt tgtgtaataa aaatggagaa    8700
gctctaaatt gttgtggttc ttttgtgaat aaaaaaatct tgattgggga aaaaaaaa     8758
```

<210> SEQ ID NO 2
<211> LENGTH: 928
<212> TYPE: DNA
<213> ORGANISM: Artificial Sequence
<220> FEATURE:
<223> OTHER INFORMATION: linc-VLDLR (NCBI Reference Sequence
NR_015375.2; Homo sapiens VLDLR antisense RNA 1 (VLDLR-AS1), long
non-coding RNA

<400> SEQUENCE: 2

```
gcctcctagg aggcgggtgg gcaaacggag acctacgcct cggggtctcc cggtgccccg     60
gctgggtccc gcccgccggc ggaggggcgc gtcctcactc accggttccg gtggcgccgc    120
tctcccgggg cgcccagcac agcgcgagca gcagccagag cgcccagagc gcggacgtgc    180
ccatggtgcc cgcctggatg gtgccgccgc cgccgccgcc gccgccgttc gctccgcacg    240
acaagttacc agtccttccg aaaggaggaa gaaggctcca agcttgatat agaagactat    300
catatgaacc agaaagggta actgaaacca agaaatgac tccagtatca agctaaagac     360
atgccttaaa ggatgaggag gagcagaaat cttaccagca aggcaagaaa gaagccgtac    420
gtgaacagcc tctgctttag gcccagaagg aaaagaagct tacaggagac aatcagtctt    480
acactcttcc atggtcacaa acaagaggtc cctggatcta caggtcatct tgcccctgaa    540
atggccctgg aaagctatgg ctgaagaatg gaggaaaaga tgactttctc tgtttcttca    600
gaccaggcat caactgggat gttgggatgt tgataaaagg acatctcatc ctttgttttc    660
tgcctatgct ttcaccatac ccattcccat gtctggtcat cacagcatcc ttcacagccc    720
ttagctgaat catgttgagt acaggatggt gtgaatatca tggtttgaat gcaaccatgg    780
tctgtcagtg tggcttgttt tttgcagccc acttagactt aagccctctt aatttcaaaa    840
ttacgttcat atgtgccaat aaagttgtcc ctacatgaac tgaaaaaaaa aaaaaaaaa     900 aaaaaaaaaa aaaaaaaaa aaaaaaa                                         928
```

<210> SEQ ID NO 3
<211> LENGTH: 651
<212> TYPE: DNA
<213> ORGANISM: Artificial Sequence
<220> FEATURE:

<223> OTHER INFORMATION: GAS5 (NCBI Reference Sequence NR_002578.2; Homo
sapiens growth arrest specific 5 (non-protein coding) (GAS5) long
non-coding RNA

<400> SEQUENCE: 3

```
tttcgaggta ggagtcgact cctgtgaggt atggtgctgg gtgcggatgc agtgtggctc      60
tggatagcac cttatggaca gttgtgtccc caaggaagga tgagaatagc tactgaagtc     120
ctaaagagca agcctaactc aagccattgg cacacaggca ttagacagaa agctggaagt     180
tgaaatggtg gagtccaact tgcctggacc agcttaatgg ttctgctcct ggtaacgttt     240
ttatccatgg atgacttgct tgggtaagga catgaagaca gttcctgtca tacctttaa      300 aggtatggag agtcggcttg actacactgt gtggagcaag ttttaaagaa gcaaaggact     360
cagaattcat gattgaagaa atgcaggcag acctgttatc ctaaactagg gtttttaatg     420
accacaacaa gcaagcatgc agcttactgc ttgaaagggt cttgcctcac ccaagctaga     480
gtgcagtggc ctttgaagct tactacagcc tcaaacttct gggctcaagt gatcctcagc     540
ctcccagtgg tctttgtaga ctgcctgatg gagtctcatg gcacaagaag attaaaacag     600
tgtctccaat tttaataaat ttttgcaatc caaaaaaaaa aaaaaaaaaa a              651
```